(12) United States Patent
Zemelman

(10) Patent No.: US 11,174,495 B2
(45) Date of Patent: Nov. 16, 2021

(54) REPORTER SYSTEM FOR DETECTING AND TARGETING ACTIVATED CELLS

(71) Applicant: BOARD OF REGENTS, THE UNIVERSITY OF TEXAS SYSTEM, Austin, TX (US)

(72) Inventor: Boris Zemelman, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 612 days.

(21) Appl. No.: 15/780,852

(22) PCT Filed: Dec. 5, 2016

(86) PCT No.: PCT/US2016/064947
§ 371 (c)(1),
(2) Date: Jun. 1, 2018

(87) PCT Pub. No.: WO2017/096363
PCT Pub. Date: Jun. 8, 2017

(65) Prior Publication Data
US 2018/0363003 A1 Dec. 20, 2018

Related U.S. Application Data

(60) Provisional application No. 62/263,326, filed on Dec. 4, 2015.

(51) Int. Cl.
| | |
|---|---|
| *C12N 15/86* | (2006.01) |
| *A61K 48/00* | (2006.01) |
| *C12N 15/113* | (2010.01) |
| *C12Q 1/6897* | (2018.01) |
| *C12N 15/63* | (2006.01) |
| *C12N 15/85* | (2006.01) |

(52) U.S. Cl.
CPC .......... *C12N 15/86* (2013.01); *A61K 48/0066* (2013.01); *C12N 15/113* (2013.01); *C12N 15/63* (2013.01); *C12Q 1/6897* (2013.01); *C12N 15/85* (2013.01); *C12N 2830/001* (2013.01); *C12N 2830/005* (2013.01); *C12N 2830/008* (2013.01); *C12N 2830/30* (2013.01)

(58) Field of Classification Search
None
See application file for complete search history.

(56) References Cited

U.S. PATENT DOCUMENTS

| | | | |
|---|---|---|---|
| 5,030,015 A | 7/1991 | Baker et al. | |
| 5,972,560 A * | 10/1999 | Kaneko | C08G 77/50 430/270.1 |
| 6,013,516 A | 1/2000 | Verma et al. | |
| 6,172,190 B1 | 1/2001 | Hunter et al. | |
| 6,251,667 B1 * | 6/2001 | Habener | C07K 14/4705 435/252.3 |
| 2004/0028653 A1 | 2/2004 | Seed et al. | |
| 2004/0146987 A1 | 7/2004 | Zdanovsky et al. | |
| 2005/0260186 A1 | 11/2005 | Bookbinder et al. | |
| 2006/0104968 A1 | 5/2006 | Bookbinder et al. | |
| 2006/0200869 A1 | 9/2006 | Naldini et al. | |
| 2008/0233146 A1 | 9/2008 | Sato | |
| 2011/0312543 A1 | 12/2011 | Khabar | |

FOREIGN PATENT DOCUMENTS

| | | | |
|---|---|---|---|
| EP | 1507865 | 7/2008 | |
| WO | WO 95/06128 | 3/1995 | |
| WO | WO 2015/175639 | 11/2015 | |
| WO | WO-2015175639 A1 * | 11/2015 | ............. A61P 33/00 |

OTHER PUBLICATIONS

Schlabach, et al. (2010) "Synthetic Design of Strong Promoters", Proceedings of the National Academy of Sciences of the United States of America, 107(6): 2538-43. (Year: 2010).*
Citovsky, Vitaly, et al. "Subcellular localization of interacting proteins by bimolecular fluorescence complementation in planta." *Journal of Molecular Biology* 362.5 (2006): 1120-1131.
Drew et al., "A High Precision Method for Activity-Dependent Neural Circuit Mapping", BRAIN Meeting, Washington, DC, Dec. 2015.
International Preliminary Report on Patentability issued in International Application No. PCT/US2016/064947, dated Jun. 14, 2018.
International Search Report and Written Opinion issued in International Application No. PCT/US2016/064947, dated Feb. 8, 2017.
Matthess, Yves, et al. "Conditional inhibition of cancer cell proliferation by tetracycline-responsive, H1 promoter-driven silencing of PLK1." *Oncogene* 24.18 (2005): 2973.
Miyazaki, Yusuke, et al. "Destabilizing domains derived from the human estrogen receptor." *Journal of the American Chemical Society* 134.9 (2012): 3942-3945.
Rim, Jong S., and Leslie P. Kozak. "Regulatory motifs for CREB-binding protein and Nfe212 transcription factors in the upstream enhancer of the mitochondrial uncoupling protein 1 gene." *Journal of Biological Chemistry* 277.37 (2002): 34589-34600.

* cited by examiner

*Primary Examiner* — Robert M Kelly

(74) *Attorney, Agent, or Firm* — Parker Highlander PLLC

(57) ABSTRACT

The present invention provides methods and compositions for labeling and/or targeting cells with increased calcium by providing a CREB reporter system. In addition, methods of treating disorders with activated cells such as brain disorders or cancer are also provided herein.

17 Claims, 9 Drawing Sheets

Specification includes a Sequence Listing.

SEQUENCE LISTING

```
<160> NUMBER OF SEQ ID NOS: 35

<210> SEQ ID NO 1
<211> LENGTH: 8
<212> TYPE: DNA
<213> ORGANISM: Artificial sequence
<220> FEATURE:
<223> OTHER INFORMATION: Synthetic construct CRE palindromic sequence

<400> SEQUENCE: 1 tgacgtca                                                              8

<210> SEQ ID NO 2
<211> LENGTH: 71
<212> TYPE: DNA
<213> ORGANISM: Artificial sequence
<220> FEATURE:
<223> OTHER INFORMATION: Synthetic construct CMV minimal promoter
```

<400> SEQUENCE: 2

```
ggtaggcgtg tacggtggga ggcctatata agcagaactc gtttagtgaa ccgtcagatc      60
gcctggagct c                                                          71
```

<210> SEQ ID NO 3
<211> LENGTH: 99
<212> TYPE: DNA
<213> ORGANISM: Artificial sequence
<220> FEATURE:
<223> OTHER INFORMATION: Synthetic construct Na/K ATPase minimal
      promoter

<400> SEQUENCE: 3

```
ggcatatgag gaggcggatc cctatcagtg atagagatct ccctatcagt gatagagagg      60
atccccggcc gccgcagcct ctgtgcggtg ggagagctc                             99
```

<210> SEQ ID NO 4
<211> LENGTH: 466
<212> TYPE: DNA
<213> ORGANISM: Artificial sequence
<220> FEATURE:
<223> OTHER INFORMATION: Synthetic construct Arc minimal promoter

<400> SEQUENCE: 4

```
gcgcagcaga gcacattagt cactcggggc tgtgaagggg cgggtccttg agggcaccca      60
cgggagggga gcgagtaggc gcggaaggcg gggcctgcgg caggagaggg cgcgggcggg     120
ctctggcgcg gagcctgggc gccgccaatg ggagccaggg ctccacgagc tgccgcccac     180
gggccccgcg cagcataaat agccgctggt gtccctatca gtgatagaga tctccctatc     240
agtgatagag agcggtttcg gtgcagaact caagcgagtt ctcccgcagc cgcagtctct     300
gggcctctct agcttcagcg gcgacgagcc tgccacactc gctaagctcc tccggcaccg     360
cacacctgcc actgccgctg cagccgccgg ctctgctccc ttccggcttc tgcctcagag     420
gagttcttag cctgttcgga gccgcagcac cgacgaccag gagctc                    466
```

<210> SEQ ID NO 5
<211> LENGTH: 398
<212> TYPE: DNA
<213> ORGANISM: Artificial sequence
<220> FEATURE:
<223> OTHER INFORMATION: Synthetic construct ratGAD2-a minimal promoter

<400> SEQUENCE: 5

```
ggtaccgaat tcctctctca tctccccacc aagctccctc tccctaaaaa tctcttgggc      60
cctttccact ttccaatctc cagactgcga ggatcacggc tactcccccc atttaacctc     120
ggcggcgcag agcacagcag cgcgtccctg cgccctgact ggaacataca aacacgcacg     180
agcactggca tacgcagaca gcacgtttcc tgtccctgtg tgacacccac cctcgtcgcg     240
ctgccgctcc agccctcgcg cggtgccctt ctcccgccac acgtactcgc acacgcacgc     300
actctcgtgc agggtcgagg caaaggcagc ttgccacagc cacttggagg cgaccagcgc     360
cagtctagca gaacccggta cccctgcagg gcggccgc                             398
```

<210> SEQ ID NO 6
<211> LENGTH: 302
<212> TYPE: DNA
<213> ORGANISM: Artificial sequence
<220> FEATURE:
<223> OTHER INFORMATION: Synthetic construct ratGAD2-b minimal promoter

<400> SEQUENCE: 6

```
ggtaccgaat tcccatttaa cctcggcggc gcagagcaca gcagcgcgtc cctgcgccct      60
gactggaaca tacaaacacg cacgagcact ggcatacgca gacagcacgt ttcctgtccc     120
tgtgtgacac ccaccctcgt cgcgctgccg ctccagccct cgcgcggtgc ccttctcccg     180
ccacacgtac tcgcacacgc acgcactctc gtgcagggtc gaggcaaagg cagcttgcca     240
cagccacttg gaggcgacca gcgccagtct agcagaaccc ggtaccctg cagggcggcc      300
gc                                                                    302
```

<210> SEQ ID NO 7
<211> LENGTH: 202
<212> TYPE: DNA
<213> ORGANISM: Artificial sequence
<220> FEATURE:
<223> OTHER INFORMATION: Synthetic construct Bidirectional CRE enhancer
      (4 CRE repeats)

<400> SEQUENCE: 7

```
gtcgacttga ctcacgggga tttccaagtc tccaccccat tgacgtcaat gggagtttgt      60
ctcgagtctc caccccattg acgtcaatgg gagtttgtag atcttctcca ccccattgac     120
gtcaatggga gtttgtctcg agtctccacc ccattgacgt caatgggagt tgttttggc     180
accaaaatca acgggagtcg ac                                              202
```

<210> SEQ ID NO 8
<211> LENGTH: 126
<212> TYPE: DNA
<213> ORGANISM: Artificial sequence
<220> FEATURE:
<223> OTHER INFORMATION: Synthetic construct Bidirectional CRE enhancer
      (2 CRE repeats)

<400> SEQUENCE: 8

```
gtcgacttga ctcacgggga tttccaagtc tccaccccat tgacgtcaat gggagtttgt      60
ctcgagtctc caccccattg acgtcaatgg gagtttgttt tggcaccaaa atcaacggga     120
gtcgac                                                                126
```

<210> SEQ ID NO 9
<211> LENGTH: 111
<212> TYPE: DNA
<213> ORGANISM: Artificial sequence
<220> FEATURE:
<223> OTHER INFORMATION: Synthetic construct Minimal promoter: CMV/TetO2
      (with 2 TET promoter operator sequences)

<400> SEQUENCE: 9

```
ggtaggcgtg tacggtggga ggcctatata agcagaactc tccctatcag tgatagagat      60
ctccctatca gtgatagaga gtttagtgaa ccgtcagatc gcctggagct c              111
```

<210> SEQ ID NO 10
<211> LENGTH: 153
<212> TYPE: DNA
<213> ORGANISM: Artificial sequence
<220> FEATURE:
<223> OTHER INFORMATION: Synthetic construct Minimal promoter: CMV/TetO4
      (with 4 TET promoter operator sequences)

<400> SEQUENCE: 10

```
ggtaggcgtg tacggtggga ggcctatata agcagaactc tccctatcag tgatagagat      60
```

```
ctccctatca gtgatagaga tctccctatc agtgatagag atctcccta t cagtgataga    120 gagtttagtg aaccgtcaga tcgcctggag ctc                                  153

<210> SEQ ID NO 11
<211> LENGTH: 125
<212> TYPE: DNA
<213> ORGANISM: Artificial sequence
<220> FEATURE:
<223> OTHER INFORMATION: Synthetic construct Minimal promoter: CMV/Van04
      (with 2 VAN promoter operator sequences)

<400> SEQUENCE: 11
ggtaggcgtg tacggtggga ggcctatata agcagaactc attggatcca atcgattgga     60
tccaatggat tggatccaat cgattggatc caatgtttag tgaaccgtca gatcgcctgg    120
agctc                                                                 125

<210> SEQ ID NO 12
<211> LENGTH: 186
<212> TYPE: DNA
<213> ORGANISM: Artificial sequence
<220> FEATURE:
<223> OTHER INFORMATION: Synthetic construct Minimal promoter: CMV/Van08
      (with 8 VAN promoter operator sequences)

<400> SEQUENCE: 12
ggtaggcgtg tacggtggga ggcctatata agcagaactc attggatcca atgcattgga     60
tccaatggat tggatccaat cgattggatc caatgatatc attggatcca atgcattgga    120
tccaatggat tggatccaat cgattggatc caatggttta gtgaaccgtc agatcgcctg    180
gagctc                                                                186

<210> SEQ ID NO 13
<211> LENGTH: 211
<212> TYPE: DNA
<213> ORGANISM: Artificial sequence
<220> FEATURE:
<223> OTHER INFORMATION: Synthetic construct Minimal promoter: CMV/Etr04
      (with 4 ETR promoter operator sequences)

<400> SEQUENCE: 13
ggtaggcgtg tacggtggga ggcctatata agcagaactc gattgaatat aaccgacgtg     60
actgttacat ttagggattg aatataaccg acgtgactgt tacatttagg gattgaatat    120
aaccgacgtg actgttacat ttagggattg aatataaccg acgtgactgt tacatttagg    180
gtttagtgaa ccgtcagatc gcctggagct c                                   211

<210> SEQ ID NO 14
<211> LENGTH: 362
<212> TYPE: DNA
<213> ORGANISM: Artificial sequence
<220> FEATURE:
<223> OTHER INFORMATION: Synthetic construct Complete
      bidirectional/bitemporal promoter (<<CRE>>)

<400> SEQUENCE: 14
ggtacccagg cgatctgacg gttcactaaa cgagttctgc ttatataggc ctcccaccgt     60
acacgcctac ccccgaattc gtcgacttga ctcacgggga tttccaagtc tccacccat    120 tgacgtcaat gggagtttgt ctcgagtctc accccattg acgtcaatgg gagtttgtag    180
atcttctcca ccccattgac gtcaatggga gtttgtctcg agtctccacc ccattgacgt    240
caatgggagt ttgttttggc accaaaatca acgggagtcg acatgcatgg gggtaggcgt    300
```

```
gtacggtggg aggcctatat aagcagaact cgtttagtga accgtcagat cgcctggagc    360
tc                                                                  362

<210> SEQ ID NO 15
<211> LENGTH: 584
<212> TYPE: DNA
<213> ORGANISM: Artificial sequence
<220> FEATURE:
<223> OTHER INFORMATION: Synthetic construct Complete
      bidirectional/bitemporal promoter ETR(<<CRE)/TET(CRE>>)

<400> SEQUENCE: 15
ggtacccagg cgatctgacg gttcactaaa ccctaaatgt aacagtcacg tcggttatat     60
tcaatcccta aatgtaacag tcacgtcggt tatattcaat ccctaaatgt aacagtcacg    120
tcggttatat tcaatcccta aatgtaacag tcacgtcggt tatattcaat cgagttctgc    180 ttataggc ctcccaccgt acacgcctac ccccgaattc gtcgacttga ctcacgggga      240
tttccaagtc tccaccccat tgacgtcaat gggagtttgt ctcgagtctc accccattg     300 acgtcaatgg gagtttgtag atcttctcca ccccattgac gtcaatggga gtttgtctcg    360
agtctccacc ccattgacgt caatgggagt tgttttggc accaaaatca cgggagtcg     420 acatgcatgg gggtaggcgt gtacggtggg aggcctatat aagcagaact ctccctatca    480
gtgatagaga tctccctatc agtgatagag atctccctat cagtgataga gatctcccta    540
tcagtgatag agagtttagt gaaccgtcag atcgcctgga gctc                    584

<210> SEQ ID NO 16
<211> LENGTH: 498
<212> TYPE: DNA
<213> ORGANISM: Artificial sequence
<220> FEATURE:
<223> OTHER INFORMATION: Synthetic construct Complete
      bidirectional/bitemporal promoter VAN(<<CRE)/TET(CRE>>)

<400> SEQUENCE: 16
ggtacccagg cgatctgacg gttcactaaa cattggatcc aatcgattgg atccaatcca     60
ttggatccaa tcgattggat ccaatgagtt ctgcttatat aggcctccca ccgtacacgc    120 ctaccccga attcgtcgac ttgactcacg gggatttcca gtctccaccc cattgacgt     180 caatgggagt ttgtctcgag tctccacccc attgacgtca atgggagttt gtagatcttc    240
tccaccccat tgacgtcaat gggagtttgt ctcgagtctc accccattg acgtcaatgg    300 gagtttgttt tggcaccaaa atcaacggga gtcgacatgc atgggggtag gcgtgtacgg    360
tgggaggcct atataagcag aactctccct atcagtgata gagatctccc tatcagtgat    420
agagatctcc ctatcagtga tagagatctc cctatcagtg atagagagtt tagtgaaccg    480
tcagatcgcc tggagctc                                                 498

<210> SEQ ID NO 17
<211> LENGTH: 596
<212> TYPE: DNA
<213> ORGANISM: Artificial sequence
<220> FEATURE:
<223> OTHER INFORMATION: Synthetic construct Complete tunable
      constitutive promoter mSYN422 Tet04

<400> SEQUENCE: 17
gtcgactctg ggaagggcaa gagtgtgtaa gtgcaagtta gcctaaggaa taggaagagg     60
ttggtaaaca gggtaggatc gtgggaggga gtttcgttac tacaggtccg gaccctcagg    120
```

```
acaagaaccc cacccccact ccccaaattg cgcatccccc gccccatca gaggggagg     180 ggaagaggtt gcggcgcggc gcatgcgcac tgtcggattc agcaccgcgg tcagagcctt   240
cgcctccgct gccggcgcgc accaccacct ccccagcacc aaaggctgac tgacgtcact   300 cactagcccct ccccaaactc ccctctcctcg ccgccttggt cgcgtccatg ctgccgtgag 360
tccagtcgga ccgcaccacg agaggtgcaa gatagggagg tgcgggcgcg accatacgct   420
ctgcggcggt cgacatgcat gggggtaggc gtgtacggtg ggaggcctat ataagcagaa   480
ctctccctat cagtgataga gatctcccta tcagtgatag agatctccct atcagtgata   540
gagatctccc tatcagtgat agagagttta gtgaaccgtc agatcgcctg gagctc      596
```

```
<210> SEQ ID NO 18
<211> LENGTH: 995
<212> TYPE: DNA
<213> ORGANISM: Artificial sequence
<220> FEATURE:
<223> OTHER INFORMATION: Synthetic contruct Complete enhanced tunable
      constitutive promoter mSYN422CMV TetO4 (CMV IE enhancer
      neuron-specific silencing element
      )

<400> SEQUENCE: 18
```

```
gcggccgcga attctattaa tagtaatcaa ttacggggtc attagttcat agcccatata    60
tggagttccg cgttacataa cttacggtaa atggcccgcc tggctgaccg cccaacgacc   120
cccgcccatt gacgtcaata atgacgtatg ttcccatagt aacgccaata gggactttcc   180
attgacgtca atgggtggag tatttacggt aaactgccca cttggcagta catcaagtgt   240
atcatatgcc aagtacgccc cctattgacg tcaatgacgg taaatggccc gcctggcatt   300
atgcccagta catgacctta tgggactttc ctacttggca gtacatctac gtattagtca   360
tcgctattac cattcagaac cacgacagc accgaattcg tcgactctgg aagggcaag    420 agtgtgtaag tgcaagttag cctaaggaat aggaagaggt tggtaaacag ggtaggatcg   480
tgggagggag tttcgttact acaggtccgg accctcagga caagaacccc accccccactc  540 cccaaattgc gcatccccg ccccatcag aggggaggg gaagaggttg cggcgcggcg     600
catgcgcact gtcggattca gcaccgcggt cagagcctcc gcctccgctg ccggcgcgca   660
ccaccacctc cccagcacca aaggctgact gacgtcactc actagccctc cccaaactcc   720
ccttcctcgc cgccttggtc gcgtccatgc tgccgtgagt ccagtcggac cgcaccacga   780
gaggtgcaag atagggaggt gcgggcgcga ccatacgctc tgcggcggtc gacatgcatg   840
ggggtaggcg tgtacggtgg gaggcctata taagcagaac tctccctatc agtgatagag   900
atctccctat cagtgataga gatctcccta tcagtgatag agatctccct atcagtgata   960
gagagtttag tgaaccgtca gatcgcctgg agctc                              995
```

```
<210> SEQ ID NO 19
<211> LENGTH: 630
<212> TYPE: DNA
<213> ORGANISM: Artificial sequence
<220> FEATURE:
<223> OTHER INFORMATION: Synthetic construct Complete tunable
      Cre-dependent promoter mSYN422 TetO4 dlx [Sac1/Pst1 RE sites
      eliminated and then introduced between 2 sets of asymmetric loxP
      sequences]
<220> FEATURE:
<221> NAME/KEY: misc_feature
<222> LOCATION: (591)..(596)
<223> OTHER INFORMATION: Sac1/Pst1 RE sites
```

<400> SEQUENCE: 19

```
gtcgactctg ggaagggcaa gagtgtgtaa gtgcaagtta gcctaaggaa taggaagagg    60
ttggtaaaca gggtaggatc gtgggaggga gtttcgttac tacaggtccg gaccctcagg   120
acaagaaccc caccccccact ccccaaattg cgcatccccc gccccatca gaggggagg    180 ggaagaggtt gcggcgcggc gcatgcgcac tgtcggattc agcaccgcgg tcagagcctt   240
cgcctccgct gccggcgcgc accaccacct ccccagcacc aaaggctgac tgacgtcact   300
cactagccct ccccaaactc cccttcctcg ccgccttggt cgcgtccatg ctgccgtgag   360
tccagtcgga ccgcaccacg agaggtgcaa gataggagg tgcgggcgcg accatacgct    420
ctgcggcggt cgacatgcat ggggtaggc gtgtacggtg ggaggcctat ataagcagaa    480
ctctccctat cagtgataga gatctcccta tcagtgatag agatctccct atcagtgata   540
gagatctccc tatcagtgat agagagttta gtgaaccgtc agatcgcctg gagcttataa   600
cttcgtatag catacattat acgaagttat                                    630
```

<210> SEQ ID NO 20
<211> LENGTH: 117
<212> TYPE: DNA
<213> ORGANISM: Artificial sequence
<220> FEATURE:
<223> OTHER INFORMATION: Synthetic construct

<400> SEQUENCE: 20

```
aacatactac gcaactctgc cctggtctca ataacttcgt ataggatact ttatacgaag    60
ttatttctgc agtttgagct cttataactt cgtataatgt atgctatacg aagttat      117
```

<210> SEQ ID NO 21
<211> LENGTH: 70
<212> TYPE: DNA
<213> ORGANISM: Artificial sequence
<220> FEATURE:
<223> OTHER INFORMATION: Synthetic construct

<400> SEQUENCE: 21

```
cctggtttac agccttcctt ccttaactcc ataacttcgt ataaagtatc ctatacgaag    60
ttatttgcag                                                           70
```

<210> SEQ ID NO 22
<211> LENGTH: 630
<212> TYPE: DNA
<213> ORGANISM: Artificial sequence
<220> FEATURE:
<223> OTHER INFORMATION: Synthetic construct Complete tunable
     Flp-dependent promoter mSYN422 TetO4 frt [Sac1/Pst1 RE sites
     eliminated and then introduced between 2 sets of asymmetric frt
     sequences]
<220> FEATURE:
<221> NAME/KEY: misc_feature
<222> LOCATION: (591)..(596)
<223> OTHER INFORMATION: Sac1/Pst1 RE sites

<400> SEQUENCE: 22

```
gtcgactctg ggaagggcaa gagtgtgtaa gtgcaagtta gcctaaggaa taggaagagg    60
ttggtaaaca gggtaggatc gtgggaggga gtttcgttac tacaggtccg gaccctcagg   120
acaagaaccc caccccccact ccccaaattg cgcatccccc gccccatca gaggggagg    180 ggaagaggtt gcggcgcggc gcatgcgcac tgtcggattc agcaccgcgg tcagagcctt   240
cgcctccgct gccggcgcgc accaccacct ccccagcacc aaaggctgac tgacgtcact   300
```

```
cactagccct ccccaaactc cccttcctcg ccgccttggt cgcgtccatg ctgccgtgag      360
tccagtcgga ccgcaccacg agaggtgcaa gatagggagg tgcgggcgcg accatacgct      420
ctgcggcggt cgacatgcat gggggtaggc gtgtacggtg ggaggcctat ataagcagaa      480
ctctccctat cagtgataga gatctcccta tcagtgatag agatctccct atcagtgata      540
gagatctccc tatcagtgat agagagttta gtgaaccgtc agatcgcctg gagcttgaag      600
ttcctattct ctagaaagta taggaacttc                                      630

<210> SEQ ID NO 23
<211> LENGTH: 117
<212> TYPE: DNA
<213> ORGANISM: Artificial sequence
<220> FEATURE:
<223> OTHER INFORMATION: Synthetic construct

<400> SEQUENCE: 23
cggtgacggt tttaagacag gtcttcgcaa gaagttccta ttcttcaaaa ggtataggaa       60
cttcttctgc agtttgagct cttgaagttc ctatactttc tagagaatag gaacttc        117

<210> SEQ ID NO 24
<211> LENGTH: 70
<212> TYPE: DNA
<213> ORGANISM: Artificial sequence
<220> FEATURE:
<223> OTHER INFORMATION: Synthetic construct

<400> SEQUENCE: 24
ctaagatatt ctaaggcgta acgcagatga gaagttccta ccttttga agaataggaa        60 cttcttgcag                                                            70

<210> SEQ ID NO 25
<211> LENGTH: 30
<212> TYPE: DNA
<213> ORGANISM: Artificial sequence
<220> FEATURE:
<223> OTHER INFORMATION: Synthetic construct 30 bp CRE spacer

<400> SEQUENCE: 25
atgggagttt gtctcgagtc tccaccccat                                       30

<210> SEQ ID NO 26
<211> LENGTH: 95
<212> TYPE: DNA
<213> ORGANISM: Artificial sequence
<220> FEATURE:
<223> OTHER INFORMATION: Synthetic construct CREhalf(1) inserted
      EcoR1/Nsi1 into unidirectional or bidirectional constructs

<400> SEQUENCE: 26
gaattcctcg agttgactca cggggatcct ctccacccca tcagcgtcaa tgggagtttg       60
ttttggcacc aaaatcaacg ggactcgaga tgcat                                 95

<210> SEQ ID NO 27
<211> LENGTH: 133
<212> TYPE: DNA
<213> ORGANISM: Artificial sequence
<220> FEATURE:
<223> OTHER INFORMATION: Synthetic contruct CREhalf(2) EcoR1/Nsi1; BamH1
      sites mark each CREhalf+spacer unit

<400> SEQUENCE: 27
gaattcctcg agttgactca cggggatcct ctccacccca tcagcgtcaa tgggagtttg       60
```

```
tggatcctct ccaccccatc agcgtcaatg ggagtttgtt ttggcaccaa aatcaacggg    120
actcgagatg cat                                                       133

<210> SEQ ID NO 28
<211> LENGTH: 171
<212> TYPE: DNA
<213> ORGANISM: Artificial sequence
<220> FEATURE:
<223> OTHER INFORMATION: Synthetic contruct CREhalf(3) EcoR1/Nsi1;
      BamH1 sites mark each CREhalf+spacer unit

<400> SEQUENCE: 28
gaattcctcg agttgactca cggggatcct ctccacccca tcagcgtcaa tgggagtttg     60
tggatcctct ccaccccatc agcgtcaatg ggagtttgtg gatcctctcc accccatcag    120
cgtcaatggg agtttgtttt ggcaccaaaa tcaacgggac tcgagatgca t             171

<210> SEQ ID NO 29
<211> LENGTH: 209
<212> TYPE: DNA
<213> ORGANISM: Artificial sequence
<220> FEATURE:
<223> OTHER INFORMATION: Synthetic construct CREhalf(4) EcoR1/Nsi1;
      BamH1 sites mark each CREhalf+spacer unit

<400> SEQUENCE: 29
gaattcctcg agttgactca cggggatcct ctccacccca tcagcgtcaa tgggagtttg     60
tggatcctct ccaccccatc agcgtcaatg ggagtttgtg gatcctctcc accccatcag    120
cgtcaatggg agtttgtgga tcctctccac cccatcagcg tcaatgggag tttgttttgg    180
caccaaaatc aacgggactc gagatgcat                                      209

<210> SEQ ID NO 30
<211> LENGTH: 247
<212> TYPE: DNA
<213> ORGANISM: Artificial sequence
<220> FEATURE:
<223> OTHER INFORMATION: Synthetic construct CREhalf(5) EcoR1/Nsi1;
      BamH1 sites mark each CREhalf+spacer unit

<400> SEQUENCE: 30
gaattcctcg agttgactca cggggatcct ctccacccca tcagcgtcaa tgggagtttg     60
tggatcctct ccaccccatc agcgtcaatg ggagtttgtg gatcctctcc accccatcag    120
cgtcaatggg agtttgtgga tcctctccac cccatcagcg tcaatgggag tttgtggatc    180
ctctccaccc catcagcgtc aatgggagtt tgttttggca ccaaaatcaa cgggactcga    240
gatgcat                                                              247

<210> SEQ ID NO 31
<211> LENGTH: 285
<212> TYPE: DNA
<213> ORGANISM: Artificial sequence
<220> FEATURE:
<223> OTHER INFORMATION: Synthetic construct CREhalf(6) EcoR1/Nsi1;
      BamH1 sites mark each CREhalf+spacer unit

<400> SEQUENCE: 31
gaattcctcg agttgactca cggggatcct ctccacccca tcagcgtcaa tgggagtttg     60
tggatcctct ccaccccatc agcgtcaatg ggagtttgtg gatcctctcc accccatcag    120
cgtcaatggg agtttgtgga tcctctccac cccatcagcg tcaatgggag tttgtggatc    180
```

```
ctctccaccc catcagcgtc aatgggagtt tgtggatcct ctccaccccca tcagcgtcaa    240 tgggagtttg ttttggcacc aaaatcaacg ggactcgaga tgcat                    285
```

<210> SEQ ID NO 32
<211> LENGTH: 160
<212> TYPE: DNA
<213> ORGANISM: Artificial sequence
<220> FEATURE:
<223> OTHER INFORMATION: Synthetic construct Phloretin regulatory domain
      and repressors; sequence includes two OttgR phloretin repressor
      binding sites

<400> SEQUENCE: 32

```
atgcatgggg gtaggcgtgt acggtgggag gcctatataa gcagaactcc agtatttaca    60
aacaaccatg aatgtaagta tattccctgc aagcagtatt tacaaacaac catgaatgta   120
agtatattcg tttagtgaac cgtcagatcg cctggagctc                         160
```

<210> SEQ ID NO 33
<211> LENGTH: 876
<212> TYPE: DNA
<213> ORGANISM: Artificial sequence
<220> FEATURE:
<223> OTHER INFORMATION: Synthetic construct TtgR-KRAB enhanced
      repressor

<400> SEQUENCE: 33

```
gagctcgcca ccatggtgag gaggaccaag gaggaggccc aggagaccag ggcccagatc    60
atcgaggccg ccgagagggc cttctacaag aggggcgtgg ccaggaccac cctggccgac   120
atcgccgagc tggccggcgt gaccaggggc gccatctact ggcacttcaa caacaaggcc   180
gagctggtgc aggccctgct ggacagcctg cacgagaccc acgaccacct ggctagggcc   240
agcgagagcg aggacgaggt ggaccccctg gctgcatga ggaagctgct gctccaggtg    300
ttcaacgagc tggtgctgga cgccaggacc aggaggatca cgagatcct gcaccacaag   360 tgcgagttca ccgacgacat gtgcgagatc aggcagcaga ggcagagcgc cgtgctggac   420
tgccacaagg gcatcaccct ggctctggcc aacgctgtga aaggggcca gctgcccggc   480 gagctggacg ctgagagggc cgctgtggcc atgttcgcct acgtggacgg cctgatcagg   540
aggtggctgc tgctgcccga cagcgtggac ctgctgggcg acgtggagaa gtgggtggac   600
accggcctgg acatgctgag gctgagcccc gccctgagga gtccggacc caagaagaag    660 aggaagctgg ccgtgagcgt gaccttcgag gacgtggccg tgctgttcac cagggacgag   720
tggaagaagc tggacctgag ccagaggagc ctgtacaggg aggtgatgct ggagaactac   780
agcaacctgg ccagcatggc cggcttcctg ttcaccaagc ccaaggtgat cagcctgctc   840
cagcagggcg aggacccctg gtccggataa ctgcag                              876
```

<210> SEQ ID NO 34
<211> LENGTH: 657
<212> TYPE: DNA
<213> ORGANISM: Artificial sequence
<220> FEATURE:
<223> OTHER INFORMATION: Synthetic construct TtgR mammalian codon-
      optimized repressor

<400> SEQUENCE: 34

```
gagctcgcca ccatggtgag gaggaccaag gaggaggccc aggagaccag ggcccagatc    60
atcgaggccg ccgagagggc cttctacaag aggggcgtgg ccaggaccac cctggccgac   120
atcgccgagc tggccggcgt gaccaggggc gccatctact ggcacttcaa caacaaggcc   180
```

```
gagctggtgc aggccctgct ggacagcctg cacgagaccc acgaccacct ggctagggcc      240
agcgagagcg aggacgaggt ggaccccctg ggctgcatga ggaagctgct gctccaggtg      300
ttcaacgagc tggtgctgga cgccaggacc aggaggatca acgagatcct gcaccacaag      360
tgcgagttca ccgacgacat gtgcgagatc aggcagcaga ggcagagcgc cgtgctggac      420
tgccacaagg gcatcaccct ggctctggcc aacgctgtga aaggggcca gctgcccggc       480 gagctggacg ctgagagggc cgctgtgtgcc atgttcgcct acgtggacgg cctgatcagg     540
aggtggctgc tgctgcccga cagcgtggac ctgctgggcg acgtggagaa gtgggtggac      600
accggcctgg acatgctgag gctgagcccc gccctgagga gtccggata actgcag         657

<210> SEQ ID NO 35
<211> LENGTH: 701
<212> TYPE: DNA
<213> ORGANISM: Artificial sequence
<220> FEATURE:
<223> OTHER INFORMATION: Synthetic construct Glia-specific promoter for
      glioblastoma targeting; GFAP promoter regions ABC1D (XmaI) GFAP
      basal promoter (SacI)

<400> SEQUENCE: 35
gcggccgcga attcaacata tcctggtgtg gagtagggga cgctgctctg acagaggctc       60
gggggcctga gctggctctg tgagctgggg aggaggcaga cagccaggcc ttgtctgcaa      120
gcagacctgg cagcattggg ctggccgccc cccagggcct cctcttcatg cccagtgaat      180
gactcacctt ggcacagaca caatgttcgg ggtgggcaca gtgcctgctt cccgccgcac      240
cccagccccc ctcaaatgcc ttccgagaag cccattgagc aggggcttg cattgcaccc       300 cagcctgaca gcctggcatc ttgggataaa agcagcacag cccctaggg gctgcccttg       360 ctgtgtggcg ccaccggcgg tggagaacaa ggctctattc agcctgtgcc caggaaaggg     420
gatcagggga tgcccaggca tggacagtgg gtggcagggg gggagaggag ggctgtctgc     480
ttcccagaag tccaaggaca caaatgggtg aggggagaac tctccccata gctgggctgc     540
ggcccaaccc cacccctca ggctatgcca gggggtgttg ccaggggcac ccgggcatcg      600
ccagtctagc ccactccttc ataaagccct cgcatcccag gagcgagcag agccagagca      660
ggttggagag gagacgcatc acctccgctg ctcgcgagct c                         701
```

REPORTER SYSTEM FOR DETECTING AND TARGETING ACTIVATED CELLS

This application is a national phase application under 35 U.S.C. § 371 of International Application No. PCT/US2016/064947, filed Dec. 5, 2016, which claims the benefit of U.S. Provisional Patent Application No. 62/263,326, filed Dec. 4, 2015, the entirety of each of which is incorporated herein by reference.

This invention was made with government support under Grant no. R21 EY026446 awarded by the National Institutes of Health. The government has certain rights in the invention.

The sequence listing that is contained in the file named "UTFBP1095WO_ST25.txt", which is 22 KB (as measured in Microsoft Windows®) and was created on Dec. 5, 2016, is filed herewith by electronic submission and is incorporated by reference herein

BACKGROUND OF THE INVENTION

1. Field of the Invention

The present invention relates generally to the fields of molecular biology and medicine. More particularly, it concerns methods and compositions for detecting and targeting activated cells.

2. Description of Related Art

Genetic access to neurons active during distinct behavioral, physiological and pathological states provides the means to directly manipulate the activity of identified cells through gene therapy. In the laboratory setting, manipulation of functionally defined cellular substrates is central to uncovering pathomechanisms of brain diseases. Currently, proteins absent from the central or peripheral nervous systems can be used to activate or silence neurons and other cells expressing such proteins. The coding information for heterologous actuator expression can be delivered using viruses, lipids or any other means for getting foreign DNA and RNA into cells. However, such methods can be applied selectively only if the cellular targets are known. Even then, means for achieving cell type-specificity of heterologous protein expression in nontransgenic organisms are largely absent. Thus, there is a lack of a system that provides the means to express actuators for selective stimulation or silencing of neurons or other cells to achieve therapeutic goals.

SUMMARY OF THE INVENTION

Embodiments of the present invention provide methods and compositions for detecting and/or targeting an activated cell. In a first embodiment, there is provided an expression vector comprising a bidirectional synthetic CRE enhancer operably linked to (i) a first promoter operably linked to a first expressible gene positioned 3' relative to the bidirectional synthetic CRE enhancer; and (ii) a second promoter operably linked to a second expressible gene positioned 5' relative to the bidirectional synthetic CRE enhancer, wherein the bidirectional synthetic CRE enhancer comprises at least 1 CRE palindromic sequences (or at least 1 CRE half site sequences having a sequence CGTCA) separated by a spacer sequence. In further embodiment there is provided an expression vector comprising a bidirectional synthetic CRE enhancer operably linked to (i) a first promoter operably linked to a first expressible gene positioned 3' relative to the bidirectional synthetic CRE enhancer; and (ii) a second promoter operably linked to a second expressible gene positioned 5' relative to the bidirectional synthetic CRE enhancer, wherein the bidirectional synthetic CRE enhancer comprises at least 2 CRE palindromic sequences (or at least 2 CRE half site sequences having a sequence CGTCA) separated by a spacer sequence. In certain aspects, upon expression of a vector of the embodiments in a eukaryotic cell, the first and the second expressible genes are expressed only in the presence of phosphorylated CREB protein (e.g., in cells that are mis-regulated, such as cancer cells or activated neurons). In certain aspects, the bidirectional synthetic CRE enhancer comprises 2 to 10 CRE palindromic sequences or 2 to 10 CRE half site sequences. In certain aspects, the bidirectional synthetic CRE enhancer comprises at least 3, 4, 5, 6, 7, 8 or 9 CRE palindromic sequences or CRE half site sequences. In particular, in some aspects, the bidirectional synthetic CRE palindromic sequences each comprise the sequence TGACGTCA (SEQ ID NO: 1). In some cases, each of the CRE palindromic sequences (or CRE half site sequences) are separated from one another by a spacer sequence. In certain aspects, the spacer sequence comprises 10 to 200 or 20 to 100 nucleotides. For example, the spacer sequence can comprise 25, 30, 35, 40 or 45 to 50 nucleotides. In certain aspects, a spacer sequence for use in a vector according to the embodiments (e.g., between the CRE palindromic sequences of a synthetic CRE enhancer) comprises a sequence having at least about 85%, 90%, 91%, 92%, 93%, 94%, 95%, 96%, 97%, 98%, 99% or 100% identity to the spacer sequence of SEQ ID NO: 25. In a further aspect, a spacer sequence for use in a vector according to the embodiments comprises at least about 10, 15, 20 or 25 contiguous nucleotides of the sequence provided as SEQ ID NO: 25.

Example bidirectional synthetic CRE enhancer elements of the embodiment are provided as SEQ ID NO: 7 (having 4 CRE palindromic sequences) and SEQ ID NO: 8 (having 2 CRE palindromic sequences). Thus, in some aspects a vector of the embodiments comprises a sequence having at least about 85%, 90%, 91%, 92%, 93%, 94%, 95%, 96%, 97%, 98%, 99% or 100% identity to the sequence of SEQ ID NOs: 7-8. In a further aspect, a vector according to the embodiments comprises at least about 25, 30, 35 or 40 contiguous nucleotides of the sequences provided as SEQ ID NOs: 7-8. Further examples of specific bidirectional vector sequence according to the embodiments are provided as SEQ ID NOs: 14-16. Thus, in some aspects a vector of the embodiments comprises a sequence having at least about 85%, 90%, 91%, 92%, 93%, 94%, 95%, 96%, 97%, 98%, 99% or 100% identity to the sequence of SEQ ID NOs: 14-16. In a further aspect, a vector according to the embodiments comprises at least about 30, 40 or 50 contiguous nucleotides of the sequences provided as SEQ ID NOs: 14-16.

Further bidirectional synthetic CRE enhancer elements of the embodiment are provided as SEQ ID NO: 27 (having 2 CRE half sites), SEQ ID NO: 28 (having 3 CRE half sites), SEQ ID NO: 29 (having 4 CRE half sites), SEQ ID NO: 30 (having 5 CRE half sites) and SEQ ID NO: 31 (having 6 CRE half sites). Thus, in some aspects a vector of the embodiments comprises a sequence having at least about 85%, 90%, 91%, 92%, 93%, 94%, 95%, 96%, 97%, 98%, 99% or 100% identity to the sequence of SEQ ID NOs: 27-31. In a further aspect, a vector according to the embodiments comprises at least about 25, 30, 35 or 40 contiguous nucleotides of the sequences provided as SEQ ID NOs:

27-31. Further examples of specific bidirectional vector sequence according to the embodiments are provided as SEQ ID NOs: 27-31.

In further aspects, the first promoter and/or the second promoter is a minimal promoter. For example, the first promoter and/or the second promoter can be selected from the group consisting of minimal broadly active promoters, such as CMV promoter, a minimal Na/K ATPase promoter, a minimal Arc promoter or minimal promoters conferring cell type-specificity, such as minimal GAD2 promoter (e.g., the ratGAD2-a or ratGAD2-b promoters). For example, in some cases a minimal promoter for use according to the embodiments comprises a sequence having at least about 85%, 90%, 91%, 92%, 93%, 94%, 95%, 96%, 97%, 98%, 99% or 100% identity to the minimal promoter sequences of SEQ ID NOs: 2-6. In a further aspect, a minimal promoter sequence for use in a vector according to the embodiments comprises at least about 50, 75, 100, 125 or 150 contiguous nucleotides of the sequences provided as SEQ ID NOs: 2-6.

In some further aspects, the first promoter and/or the second promoter for use in a vector of the embodiments includes genetic elements that confer is a cell or tissue type-specificity. For example, in some aspects, a promoter comprises a cell-type specific silencing element. In particular aspects, the first promoter and/or the second promoter can be neuron specific promoter or comprises a neuron-specific silencing element, limiting expression to neuronal cells. In some aspects, the first promoter and/or the second promoter is a TATA box-containing promoter.

In some aspects, the first promoter and/or the second promoter is positioned 10 to 200 nucleotides from the bidirectional synthetic CRE enhancer. In further aspects, the first promoter and/or the second promoter is positioned about or at least about 20, 25, 30, 35, 40, 45, 50, 55, 60, 65, 70 or 75 to 100 nucleotides from the bidirectional synthetic CRE enhancer.

In certain aspects, the first promoter and/or the second promoter comprises an operator element that can support ligand-dependent expression gating. As used herein an "operator element" refers to a DNA sequence that can bind to a polypeptide (also referred to herein as an operator binding element) in a ligand dependent manor, such that the polypeptide affects promoter activity (e.g., the polypeptide can bind to operator element and block transcriptional activity). For example, a first promoter and/or second promoter of the embodiments can comprise 2-10 operator elements. For example, the promoter can comprise 2, 3, 4, 5, 6, 7 or 8 repeats of an operator element. In some aspects, a polypeptide that binds to an operator element can further comprise a trans-silencing domain from human kox-1 protein. In some aspects, the first promoter and/or the second promoter comprise different operator elements that can support ligand-dependent expression gating. In some aspects, the operator element is positioned 7-20 nucleotides (e.g., 8, 9 or 10 nucleotides) after the TATA box of the first promoter and/or the second promoter. In particular, the first promoter and/or the second promoter comprise a TET, VAN, ETR or OttgR operator element. Examples of promoters comprising operator elements include the sequences provided as SEQ ID NO: 9 (a CMV promoter with 2 TET operators); SEQ ID NO: 10 (a CMV promoter with 4 TET operators); SEQ ID NO: 11 (a CMV promoter with 2 VAN operators); SEQ ID NO: 12 (a CMV promoter with 8 VAN operators); SEQ ID NO: 13 (a CMV promoter with 4 ETR operators), SEQ ID NO: 32 (a CMV promoter with two OttgR operators phloretin), SEQ ID NO: 33 (a TtgR-KRAB enhanced repressor) or SEQ ID NO: 34 (TtgR mammalian codon-optimized repressor). In some cases, operators can include or not include a KRAB element. In certain aspects, a first and/or second promoter of the embodiments comprises a sequence having at least about 85%, 90%, 91%, 92%, 93%, 94%, 95%, 96%, 97%, 98%, 99% or 100% identity to the promoter sequences of SEQ ID NOs: 9-13 or 32-34. In a further aspect, a promoter sequence for use in a vector according to the embodiments comprises at least about 50, 75, 100, 125 or 150 contiguous nucleotides of the sequences provided as SEQ ID NOs: 9-13 or 32-34.

In certain aspects, the first expressible gene and/or the second expressible gene encode an inhibitory nucleic acid. For example, the inhibitory nucleic acid can be an anti-sense RNA or DNA, a small interfering RNA (siRNA), or a precursor thereof, a short hairpin RNA (shRNA) or micro RNA (miRNA). In further aspects, the first expressible gene and/or the second expressible gene encodes a reporter polypeptide, an ion channel polypeptide, a cytotoxic polypeptide, an enzyme, a cell reprogramming factor, a drug resistance marker, a drug sensitivity marker, a suicide gene (e.g., a herpesvirus thymidine kinase) or a therapeutic polypeptide. For example, the reporter polypeptide is a fluorescent or luminescent polypeptide. In particular, the enzyme polypeptide is a recombinase or a transposase. In some aspects, the recombinase is a Cre, Flp or Dre recombinase. In certain aspects, the cytotoxic polypeptide is gelonin, a granzyme, a caspase, Bax, Apo-1, AIF, TNF-alpha, bacterial clostridium (e.g., botulinum or tetanus) neurotoxin catalytic subunit, or a diphtheria toxin catalytic subunit. In some aspects, the first expressible gene and/or the second expressible gene encode a polypeptide that includes a destabilization domain, such as a domain that targets the encoded polypeptide to the proteasome. In some aspects, the gene can encode a reporter polypeptide or a recombinase including one or more (e.g., 2, 3, 4 or more) domain(s) from an estrogen receptor (ER) or progesterone receptor (PR) polypeptide.

In some aspects, the first expressible gene and the second expressible gene encode polypeptides that are active only when expressed together in the same cell. For example, the first expressible gene and the second expressible gene encode two portions of a fluorescent polypeptide that only fluoresce when co-expressed in the same cell.

In certain aspects, the expression construct further comprises an expression cassette that encodes a ligand-binding polypeptide that binds to an operator element of a promoter of the embodiments in a ligand-dependent manner. In some aspects, the encoded polypeptide comprises a trans-silencing domain from human kox-1 polypeptide. For example, the ligand-binding polypeptide can be TetR, MphR, VanR or TtgR. In some aspects, expression of the ligand-binding polypeptide is under the control of an inducible promoter, such that the level of expression of the ligand-binding polypeptide can be controlled. In further aspects, expression of the ligand-binding polypeptide is under the control of a constitutive promoter. Example promoters that may be used according to the embodiments include those provided as SEQ ID NOs: 17 (a tunable constitutive promoter), 18 (a mouse synapsin promoter with a CMV enhancer and a neuron-specific silencing element), 19 (a promoter that provides gene expression only in the presence of Cre recombinase) and 22 (a promoter that provides gene expression only in the presence of Flp recombinase) and SEQ ID NO: 35 (a glia-specific promoter, e.g., for targeted expression in glia). Thus, in some aspects, a second vector of the embodiments comprises a ligand-binding polypeptide (or operator binding element) coding sequence operably linked to a promoter having at least about 85%, 90%, 91%, 92%, 93%, 94%, 95%, 96%, 97%, 98%, 99% or 100% identity to the promoter sequences of SEQ ID NOs: 17, 18, 19, 22 or 35. In a further aspect, a promoter sequence comprises at least about 50, 75, 100, 125 or 150 contiguous nucleotides of the sequences provided as SEQ ID NOs: 17, 18, 19, 22 or 35.

In some aspects, the vector is a plasmid expression vector or an episomal expression vector. In particular, the vector is a viral expression vector. For example, the viral vector is an adenovirus, adeno-associated virus (AAV), retrovirus, herpesvirus, lentivirus, poxvirus or papiloma virus expression vector. In certain preferred aspects, the vector is an AAV vector, such as an AAV2 vector. In further aspect, the AAV vector comprises ITRs from an AAV2, but coat preoteins from a different AAV serotype, such as AAV 1, 5, 7, 8, 9 or an AV with an engineered coat not found in nature.

In a further embodiment, there is provided a host cell comprising an expression vector provided herein. For example, the host cell can be a bacterial cell, a eukaryotic cell, a mammalian cell, a neuron, or a cancer cell. In certain aspects, the expression vector is maintained in the cell as a plasmid or episome. In some aspects, the expression vector is integrated into the genome of the cell. In certain aspects, there is a single copy of the expression vector is integrated into the genome of the cell. In further aspects, the cell comprises 2, 3, 4, 5 or more integrated copies of the vector.

In some aspects, the host cell further comprises at least a second expression vector. In certain aspects, the second expression vector encodes an expression cassette that encodes a ligand-binding polypeptide that binds to an operator element of a promoter in a ligand-dependent manner. In some aspects, the encoded polypeptide comprises a trans-silencing domain from human kox-1 polypeptide. For example, the ligand-binding polypeptide can be TetR, MphR, VanR or TtgR. In some aspects, expression of the ligand-binding polypeptide is under the control of an inducible promoter, such that the level of expression of the ligand-binding polypeptide can be controlled. In certain aspects, the host cell comprises a known number of integrated or episomal copies of an expression vector encoding a ligand-binding polypeptide (i.e., that provides a known level of expression of the ligand-binding polypeptide). In certain aspects, the host cell comprises sufficient levels of a ligand-binding polypeptide to bind to all operator elements in promoters comprised in the cell.

In another embodiment, there is provided a method of assessing the status of a cell comprising: (a) expressing in the cell a vector provided herein; and (b) detecting the expression of said first expressible gene and/or said second first expressible gene, thereby assessing the status of the cell. In some aspects, one of said first expressible gene or said second expressible gene encodes a fluorescent or luminescent polypeptide and wherein detecting the expression comprises imaging the cell to detect expression of the fluorescent or luminescent polypeptide. In some aspects, the gene product of the first expressible gene and second first expressible gene are detected at different time points, such as before and after treatment of the cells with a test agent. In some aspects, the method further comprises contacting the cell with a substrate that facilitates luminescence of an expressed polypeptide (e.g., luciferin). In certain aspects, the cell is ex vivo. In other aspects, the cell is in vivo. In particular aspects, the cell is in a mammalian cell. In some aspects, one or both of said first promoter or said second promoter comprises operator elements that provide promoter expression gating. In certain aspects, the method further comprises contacting the cell with a ligand that regulates expression gating in promoters have operator elements. Thus, in some aspects, the cell further comprises at least a second vector encoding ligand-binding polypeptide that binds to an operator element of a promoter in a ligand-dependent manner.

In yet another embodiment, there is provided a method of treating a mis-regulated cell comprising expressing in the cell a vector provided herein, wherein said first expressible gene and/or second expressible gene encodes a therapeutic gene product. In some aspects, one of said first expressible gene or said second expressible gene encodes a fluorescent or luminescent polypeptide (e.g., to monitor cell status vis-a-vis activity of therapeutic gene product). In certain aspects, the cell is ex vivo. In other aspects, the cell is in vivo. In particular, the cell is in a mammalian cell. In some aspects, one or both of said first promoter or said second promoter comprises operator elements that provide promoter expression gating. In certain aspects, the method further comprises contacting the cell with a ligand that regulates expression gating in promoters have operator elements. Thus, in some aspects, the cell further comprises at least a second vector encoding ligand-binding polypeptide that binds to an operator element of a promoter in a ligand-dependent manner. In some aspects, the cell is a cancer cell. In certain aspects, the cell is a neuron cell.

A further embodiment provides a method of selectively killing a cell comprising expressing in the cell a vector provided herein, wherein said first expressible gene and/or second expressible gene encodes a cytotoxic gene product. In some aspects, one of said first expressible gene or said encodes a fluorescent or luminescent polypeptide (e.g., to monitor cell status vis-a-vis activity of therapeutic gene product). In certain aspects, the cell is ex vivo. In other aspects, the cell is in vivo. In particular, the cell is a mammalian cell. In some aspects, one or both of said first promoter or said second promoter comprises operator elements that provide promoter expression gating. In certain aspects, the method further comprises contacting the cell with a ligand that regulates expression gating in promoters have operator elements. Thus, in some aspects, the cell further comprises at least a second vector encoding ligand-binding polypeptide that binds to an operator element of a promoter in a ligand-dependent manner. In some aspects, the cell is a cancer cell. In certain aspects, the cell is a neuron cell.

Thus, in some aspects, a ligand can be applied to cell to control promoter expression gating (e.g., that regulates an operator binding element). For example, the ligand can comprise, without limitation, doxycycline, erythromycin, vanillic acid, phloretin or a derivative thereof. In some aspects, the cell is in vivo and the ligand is administered locally or systemically. In certain aspects, the ligand is inactivated by a chemical modification. In particular aspects, the ligand can be activated by the application of light to cleave off the inactivating chemical modification(s). Thus, by controlling the level of either operator binding (e.g., controlling the expression level) or by controlling the level of active (unmodified) ligand applied to cells, precise control of expression from promoter having operator elements can be achieved.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
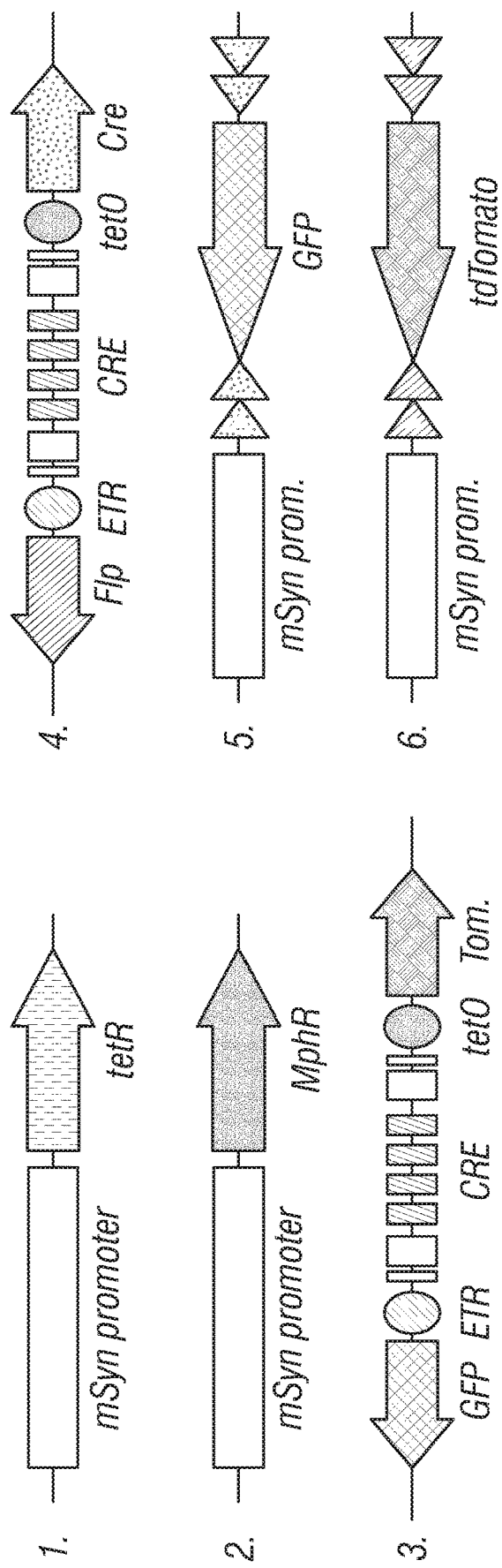
FIG. 1: Schematics of exemplary expression cassettes of the embodiments. Constructs 1 and 2 express the repressor molecules TetR and MphR. Constructs 3 and 4 are examples of the bidirectional CREB activity sensor. In 3 and 4, fluorophore (GFP and tdTomato) or recombinase (Cre and Flp) expression is regulated ETR and tetO operons. Constructs 5 and 6 encode Cre- and Flp-dependent reporters to be used with construct 4.
Figure 2A:
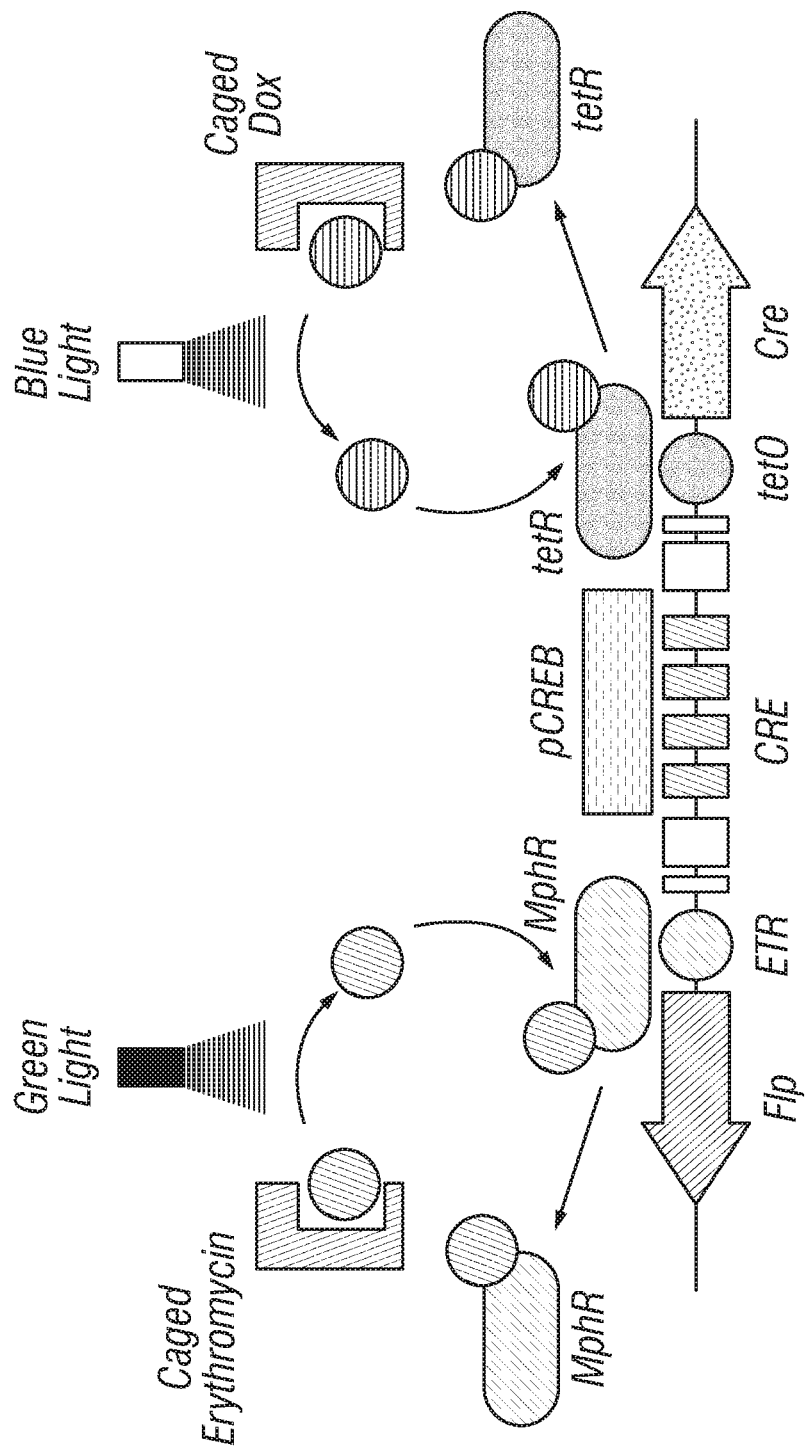
FIGS. 2A-2B: Approaches for light-mediated tagging of active neurons. (A) Green light uncages erythromycin, which relieves Flp (or GFP) from MphR-mediated repression. Blue light uncages doxycycline, which relieves Cre (or tdTomato) from TetR-mediated repression. (B) When used with construct 4, green and blue light enable permanent expression of different fluorophores or other heteroproteins.
Figure 2B:
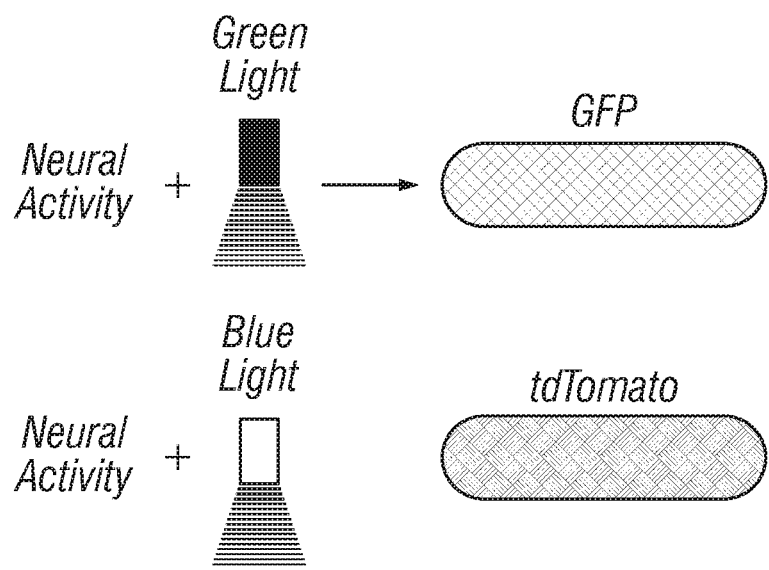

The central goal of clinical interventions that treat psychological and physiological maladies is to selectively eliminate or disrupt the function of diseased cells. This goal is predicated on being able to identify and access such cells, reliably distinguishing them from non-compromised cells nearby. No general in vivo method currently exists for achieving either requirement. The present invention overcomes challenges associated with current technologies by providing an expression construct for in vivo use that can detect fluctuations in intracellular calcium. Calcium concentration change is a prominent feature of cellular activation that, among other consequences, modifies gene expression in response to environmental signals. Calcium rises in stimulated neurons, and elevated calcium precedes neurodegeneration, as in Alzheimer's disease. Calcium also rises in smooth muscle cells at onset of pulmonary disease, at inception of tumorigenesis of prostate cells, and in numerous other instances of altered cell function. The calcium sensitive system provided herein can be used in two independent, but complementary ways: (1) to tag cells displaying altered function, and (2) to treat such cells using genetically encoded therapeutic agents. In particular, the expression construct comprises a bidirectional synthetic CRE enhancer operably linked to promoters controlling the expression of genes such as those encoding a reporter polypeptide, an ion channel polypeptide, a cytotoxic polypeptide, an enzyme, a cell reprogramming factor, a drug resistance marker or a therapeutic polypeptide. In addition, the expression construct can be regulated by promoter gating elements such as TetR, TtgR or MphR.

Thus, the CRE expression construct provided herein can be used to express proteins, such as toxin subunits, to ablate cells that may be focal points of disease, such as degenerating neurons, even when their exact locations are undetermined. Thus, the system represents a highly original, powerful and uniquely personalized approach to fighting a broad range of diseases including diseases of the brain.

I. Definitions

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an ori for EBV includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner, et. al., 2008.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Identity" refers to the percent of identity between two polynucleotides or two polypeptides. The correspondence between one sequence and another can be determined by techniques known in the art. For example, percent identity can be determined by a direct comparison of the sequence information between two polypeptide molecules by aligning the sequence information and using readily available computer programs.

A "suicide gene" "lethality gene" or "cytotoxic gene" is a nucleic acid coding for a product, wherein the product causes cell death by itself or in the presence of other compounds. A representative example of such a therapeutic nucleic acid (suicide gene) is one which codes for thymidine kinase of herpes simplex virus.

As used herein "prodrug" means any compound useful in the methods of the present invention that can be converted to a toxic product, i.e. toxic to tumor cells. The prodrug is converted to a toxic product by the gene product of the therapeutic nucleic acid sequence (suicide gene) in the vector useful in the method of the embodiments.

II. Bidirectional CREB Reporter

A. CREB Expression Construct

The core enhancer of the bidirectional CREB expression construct of the present invention comprises tandem CREB (cAMP response element binding protein) binding sites (also known as CRE sites). Cyclic AMP is an intracellular second messenger utilized by many GPCRs to promote the phosphorylation of certain cellular proteins, including CREB. CREB is also phosphorylated in response to changes in cytosolic calcium. The cAMP-responsive transcriptional element (CRE) is a palindromic consensus DNA sequence, TGACGTCA (SEQ ID NO:1). This sequence functions as a DNA binding motif specific for CREB. Phosphorylated CREB can promote gene expression when bound to CRE elements. Normally, phosphorylated CREB must function in a coordinated fashion with additional transcription factors. However, in this synthetic construct, non-CREB binding sites are absent. The core enhancer can have a variable number of CRE sites for reporter sensitivity, such as 2, 3, 4, 5, 6, 7, 8, 9, 10 or more palindromic CRE sites. In particular, the CRE sites are separated by spacer sequences about 10 to 200 nucleotides in length, such as 20 to 100 nucleotides. In particular, the expression construct has 4 CRE sites. The reporter is flanked by minimal promoters optionally containing bacterial protein binding sites for independent regulation of activity-dependent gene expression in each direction from the core enhancer.

1. Expressible Genes

The CREB expression construct comprises at least one expressible gene that can be expressed in either direction from the core promoter. In certain aspects, the first expressible gene and/or the second expressible gene encodes an inhibitory nucleic acid, a reporter polypeptide, an ion channel polypeptide, a cytotoxic polypeptide, an enzyme, a cell reprogramming factor, a drug resistance marker or a therapeutic polypeptide.

For example, the heterologous protein can be a reporter polypeptide such as a fluorescent, bioluminescent, or chemiluminescent protein for labeling and detection of activated cells. Any fluorescent, bioluminescent, or chemiluminescent protein known in the art can be used with the CREB expression construct. A variety of reporter genes can be used which are capable of generating a detectable signal. A variety of reporter genes are contemplated, including, but not limited to Green Fluorescent Protein (GFP), enhanced Green Fluorescent Protein (eGFP), Blue Fluorescent Protein (BFP), Cyan Fluorescent Protein (CFP), Yellow Fluorescent Protein (YFP), firefly luciferase, renilla luciferase (RUC), β-galactosidase, CAT (chloramphenicol acetyltransferase), alkaline phosphatase (AP), horseradish peroxidase (HRP), and tdTomato. The reporter proteins can have degradation signals to alter their half-life such as described in U.S. Patent Publication No. US20040146987, incorporated herein by reference.

Additionally, the expression construct can comprise elements of a bipartite system to increase system selectivity. One example is a split GFP molecule, where each part is expressed in a different direction from the promoter. Both parts must be made in the same cells for fluorescence to be detected, helping to separate cells that are transiently stimulated from ones that are persistently stimulated, reducing the likelihood of detecting false positives.

In some aspects, the enzyme polypeptide is a recombinase or transposase. For example, the recombinase can be a Cre recombinase, Flp recombinase, Dre recombinase, or Hin recombinase. The expression construct can comprise recombinases (with or without degradation tags and/or regulatory domains), such that the transient recombinase expression will enable constitutive expression of another protein. The recombinases can additionally be regulated by engineered hormone receptor binding domains, such as from human progesterone and estrogen receptors, and activated transiently by the respective ligands that are administered locally or systemically.

In certain aspects, gene for expression in a vector of the embodiments is an inhibitory nucleic acid. For instance, the inhibitory nucleic acid can be an anti-sense DNA or RNA, a small interfering RNA (siRNA), a short hairpin RNA (shRNA) or micro RNA (miRNA). Accordingly, the construct can comprise an RNAi expression cassette. The expression cassette can comprise the coding regions of a gene(s) that is transcribed in vivo to shRNA. The shRNA oligonucleotide design usually comprises a target sense sequence (e.g., a 19-base target sense sequence), a hairpin loop (e.g., 7-9 nucleotides), a target antisense sequence (e.g., a 19-base target antisense sequence) and a RNA Pol II terminator sequence. For example, the hairpin loop can be 5'-TTCAAGAGA-3' (Sui et al., 2002). The RNA Pol III terminator sequence is usually a 5-6 nucleotide poly(T) tract.

The construct can comprise a lethality or suicide polypeptide such as a cytotoxic polypeptide. A lethality polypeptide is a polypeptide that will cause the cell to expire through apoptosis or necrosis. Generally, a lethality polypeptide could include a toxin polypeptide, an apoptotic cell signal, or a dysregulating event. For example, an exogenous a thymidine kinase (such as from herpes virus) or a protease (e.g., an enzymatically active caspase) gene can be used as the lethality polypeptide. Other cytotoxic polypeptides include, without limitation, gelonin, Caspase 9, Bax, bacterial xanthine/guanine phosphoribosyltransferase gpt, coda, fcyl, a granzyme, Apo-1, AIF, TNF-alpha, or a diphtheria toxin subunit. The construct can comprise a suicide protein to ablate activated cells such as thymidine kinase, nitroreductase, or other enzyme or functional fragment thereof known as applicable for a similar purpose. The coupling product can penetrate into cells which are to be treated with (in the case of thymidine kinase) ganciclovir or another drug (prodrug) of the same family, so that the prodrug is converted in the cells containing the 'suicide gene' product to an active form to kill the cells. For example, the suicide gene can be caspase 9, herpes simplex virus, herpes virus thymidine kinase (HSV-tk), cytosine deaminase (CD) or cytochrome P450.

Suitable examples of useful known suicide genes and corresponding pro-drugs include thymidine kinase (suicide gene) and ganciclovir/aciclovir (prodrug), nitroreductase (suicide gene) and CB1954 (prodrug), and cytosine deaminase (suicide gene) and 5-fluorocytosine (prodrug).

2. Promoter/Enhancers

The expression constructs provided herein comprise promoters to drive expression of the expressible genes such as the reporter proteins, recombinases and/or cytotoxic polypeptides. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. In certain aspects, the promoter is positioned about 10 to 200 nucleotides, such as 20 to 100 nucleotides, from the bidirectional synthetic CRE enhancer. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (CRE), serum response element promoter (SRE), phorbol ester promoter (TPA) and response element promoters (TRE) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007).

Tissue-specific promoter may be desirable as a way to identify aberrant cells. Cell type-specific enhancers can be used to narrow the range of cells in which stimulation will trigger protein expression. To increase both specificity and activity, the use of cis-acting regulatory elements has been contemplated. For example, a neuron-specific promoter may be used. In particular, the promoter is for synapsin I, calcium/calmodulin-dependent protein kinase II, tubulin alpha I, neuron-specific enolase or platelet-derived growth factor beta chain.

In certain aspects, methods of the invention also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

3. Gating Elements

There are several bacterial transcriptional regulators known in the art that can be used with the expression construct of the present invention. The construct can comprise a ligand-inducible or ligand-repressible gating element. Several constructs are available for expressing gates at different levels. In some constructs, the gates have been modified with an additional transcriptional repressor domain to enhance gating. For example, the gates can comprise humanized versions of TetR, MphR, TtgR and VanR bacterial proteins along with their respective DNA binding sites; the ligands of which are doxycycline, erythromycin, phloretin and vanillic acid, respectively. Thus, the expression construct would comprise the DNA binding sites for the bacterial repressor proteins such as a TetO or ETR element. The repressors can be TetR homologs such as AcrR, AmtR, ArpA, BM3R1, BarA, BetI, EthR, FarA, HapR, HlyllR, IcaR, LmrA, LuxT, McbR, MphR, MtrR, MtrR, PhlF, PsrA, QacR, ScbR, SmcR, SmeT, TtgR, TylP, UidR, or VanR. The operator sequences recognized by the TetR homolog repressors have been previously identified. These operators range 16-55 bp in length, and typically contain inverted repeat sequences.

An orthogonal ligand is needed to displace each expression gate. The ligand can be delivered in photocaged form, requiring light to uncage the ligand in order to enable heterologous protein expression. The requirement for both light and activity aids the regulation of protein expression. Ligands can also be administered locally or systemically. Gating can tune protein expression either by varying the quantity of gate or by achieving saturating gate binding to promoter sites and then titrating ligand to achieve desired reporter sensitivity. The use of gate is not required, but will be beneficial in certain situations, such as when the timing and/or level of heterologous protein expression must be modulated.

4. Vectors

One of skill in the art would be well-equipped to construct the bidirectional CREB reporter vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors (e.g., an AAV2/1 vector), simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors.

a. Viral Vectors

Viral vectors may be provided in certain aspects of the present invention. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Retroviruses have promise as gene delivery vectors due to their ability to integrate their genes into the host genome, transfer a large amount of foreign genetic material, infect a broad spectrum of species and cell types, and be packaged in special cell-lines (Miller, 1992).

In order to construct a retroviral vector, a nucleic acid is inserted into the viral genome in place of certain viral sequences to produce a virus that is replication-defective. In order to produce virions, a packaging cell line containing the gag, pol, and env genes—but without the LTR and packaging components—is constructed (Mann et al., 1983). When a recombinant plasmid containing a cDNA, together with the retroviral LTR and packaging sequences, is introduced into a special cell line (e.g., by calcium phosphate precipitation), the packaging sequence allows the RNA transcript of the recombinant plasmid to be packaged into viral particles, which are then secreted into the culture medium (Nicolas and Rubenstein, 1988; Temin, 1986; Mann et al., 1983). The medium containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

b. Episomal Vectors

The use of plasmid- or liposome-based extra-chromosomal (i.e., episomal) vectors may be also provided in certain aspects of the invention. Such episomal vectors may include, e.g., oriP-based vectors, and/or vectors encoding a derivative of EBNA-1. These vectors may permit large fragments of DNA to be introduced unto a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Other sources of episome-base vectors are also contemplated, such as yeast ARS, adenovirus, SV40, or BPV.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also may include markers, such as detectable and/or selection markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

c. Transposon-Based System

In certain aspects, the delivery of the bidirectional CREB reporter can use a transposon-transposase system. For example, the transposon-transposase system could be the well known Sleeping Beauty, the Frog Prince transposon-transposase system (for a description of the latter, see, e.g., EP1507865), or the TTAA-specific transposon PiggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

In particular embodiments, the constructs (e.g., the multi-lineage construct) provided in the present invention use a PiggyBac expression system. PiggyBac (PB) DNA transposons mobilize via a "cut-and-paste" mechanism whereby a transposase enzyme (PB transposase), encoded by the transposon itself, excises and re-integrates the transposon at other sites within the genome. PB transposase specifically recognizes PB inverted terminal repeats (ITRs) that flank the transposon; it binds to these sequences and catalyzes excision of the transposon. PB then integrates at TTAA sites throughout the genome, in a relatively random fashion. For the creation of gene trap mutations (or adapted for generating transgenic animals), the transposase is supplied in trans on one plasmid and is co-transfected with a plasmid containing donor transposon, a recombinant transposon comprising a gene trap flanked by the binding sites for the transposase (ITRs). The transposase will catalyze the excision of the transposon from the plasmid and subsequent integration into the genome. Integration within a coding region will capture the elements necessary for gene trap expression. PB possesses several ideal properties: (1) it preferentially inserts within genes (50 to 67% of insertions hit genes) (2) it exhibits no local hopping (widespread genomic coverage) (3) it is not sensitive to over-production inhibition in which elevated levels of the transposase cause decreased transposition 4) it excises cleanly from a donor site, leaving no "footprint," unlike Sleeping Beauty.

5. Other Regulatory Elements a. Initiation Signals and Linked Expression

A specific initiation signal also may be used in the expression constructs provided in the present invention for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements or protease 2A/cleavage sites are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

b. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

c. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

B. Delivery of CREB Expression Construct

Introduction of a nucleic acid, such as DNA or RNA, into the host cells may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

In certain aspects, bidirectional expression constructs of the embodiments are comprised in viral vectors, such as an AAV vector. Thus, in some aspects, the vectors can be delivered to target cells by transducing the cells with the viral vector itself.

1. Liposome-Mediated Transfection

In a certain embodiment of the invention, a nucleic acid may be introduced to the host cell by liposome-mediated transfection. In this method, the nucleic acid is entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen). The amount of liposomes used may vary based upon the nature of the liposome as well as the cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

III. Methods of Use

A. Detection or Targeting of Activated Cells

In some embodiments, the present invention provides a method of assessing the status of a cell by expressing the expression vector in a host cells and detecting the expression of the first and/or second expressible gene to determine the status of the cell. Detection of the expressible gene can comprise using an instrument selected from the group consisting of a microscope, a luminometer, a fluorescent microscope, a confocal laser-scanning microscope, and a flow cytometer.

The expression construct provided herein can also be used to target a dysregulated or aberrant cell by expressing the construct in a host cell such that the first and/or second expressible gene encodes a therapeutic or cytotoxic gene product.

The expression construct can be administered to the cell in vivo or ex vivo, and the host cell can be a bacterial, eukaryotic, mammalian, neuron or cancer cell. In certain aspects, the expression construct is administered in combination with a ligand for the gating element such as doxycycline, erythromycin, phloretin or vanillic acid.

1. Nervous System

In some embodiments, the CREB expression construct of the present invention can tag neurons activated during cognitive and physiological states, including fear, hunger, pain, depression, anxiety, addiction, as well as those affected by disease, such as stroke (or other brain injury), neurodegeneration and epilepsy. Tagging neurons, for example those in the brain supporting focal epilepsies, or those degenerating at the onset of Alzheimer's and similar diseases, or those in the peripheral or central nervous system supporting chronic pain, enables such neurons to be visualized and eliminated using traditional imaging and surgical techniques, while sparing nearby healthy neurons.

Alternatively, neuronal tagging during recovery from stroke, other brain injury, or peripheral neuron injury could aid in monitoring healing. In addition, neurons tagged in animal models of human diseases can be isolated and used to screen compound libraries for the ability to selectively alter the function tagged neurons, but not healthy neurons; candidate drugs emerging from such screens could then be tested in human subjects.

In certain embodiments, tagging of neurons activated by candidate drugs administered to experimental animals or human subjects in clinical trials could establish and refine the complement of cells those drugs target, enabling more specific and more personalized treatments to be developed.

Particular brain diseases include brain tumors, Alzheimer's disease, Parkinson's disease, Huntington's disease, lateral amyotrophic sclerosis, neurodegenerative and neurometabolic disorders, chronic brain infections (e.g. HIV, measles, etc.), pituitary tumors, spinal cord degeneration (both inherited and traumatic), spinal cord regeneration, autoimmune diseases (e.g. multiple sclerosis, Guillain Barre syndrome, peripheral neuropathies, etc.) and any other diseases of the brain known to persons skilled in the art.

2. Cancer

Cell that have become transformed, such as in cancers of the prostate and skin, among many others, are characterized by elevated intracellular calcium. Some researchers postulate that gene expression changes linked to elevated calcium contribute to disease progression and promote angiogenesis. The reporter systems provided herein can be used in two ways to detect and eliminate tumors, similar to those described for brain disorders. In some embodiments, the reporter can tag cells that have become transformed. The labeled cells can then be eliminated using existing surgical techniques. In addition, the reporter can be used as a diagnostic tool to stage disease progression, to evaluate treatment efficacy, and to screen treatment options.

Transformed cells labeled using the reporter system can be harvested and genetically profiled to identify intrinsic changes responsible for the transformed phenotype. In this case the sampled cell population need not be homogeneous, as would be true for advanced tumors, but can include intermixed healthy and transformed cells, since reporter is selective for transformed cells. Detailed information about transformed cell phenotype at an early stage of the disease may aid treatment selection and improve its efficacy.

When the reporter is functionally linked to an enzyme or toxin subunit that can eliminate cells in which it is expressed, the reporter can be a vehicle for highly selective gene therapy. The DNA can be delivered locally using viruses, lipids or any other effective means for getting foreign DNA and RNA into cells, including in an ointment for treatment of skin disorders. Unlike existing treatments that may be toxic to a variety of healthy and compromised cells, the reporter system can be tuned to eliminate diseased cells with minimal impact on nearby healthy cells.

Exemplary cancer cells that can be detected or targeted by the CREB reporter system include a gastrointestinal cancer cell, a hepatobiliary cancer cell, a gall bladder cancer cell, a pancreatic cancer cell, a lung cancer cell, a mesothelioma cancer cell, a bladder cancer cell, a prostate cancer cell, a breast cancer cell, a head cancer cell, a neck cancer cell, a thyroid cancer cell, a uterine cancer cell, a cervix cancer cell, a uterine-cervix cancer cell, a blood cancer cell, a white blood cancer cell, a bone marrow cancer cell, a pleural cancer cell, and a pleural fluid cancer cell.

3. Administration

The CREB reporter/operator binding elements (bacterial repressor proteins) and/or ligand(s) (e.g., bacterial repressor protein ligand) may be administered in any suitable manner known in the art. For example, the CREB reporter/operator binding elements and/or ligand(s) may be administered sequentially (at different times) or concurrently (at the same time). The order of addition and quantity of each will determine reporter sensitivity and the level of heterologous protein expression. The CREB reporter/operator binding elements and/or ligand(s) may be administered by the same route of administration or by different routes of administration such as intravenously, intramuscularly, subcutaneously, topically, orally, transdermally, intraperitoneally, intraorbitally, by implantation, by inhalation, intrathecally, intraventricularly, or intranasally. An effective amount of the CREB reporter, operator binding elements and ligand(s) may be administered for detection or ablation of activated cells. For ablation of activated cells, the appropriate dosage may be determined based on the type of disease to be treated, severity and course of the disease, the clinical condition of the individual, the individual's clinical history and response to the treatment, and the discretion of the attending physician. The dose may be administered as a single dose or as multiple doses (e.g., 2 or 3 doses), such as infusions.

Pharmaceutical compositions and formulations of the CREB reporter/operator binding elements and/or ligand(s) can be prepared by mixing the active ingredients (such as a nucleic acid or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Test Compound Screening

The CREB reporter system of this invention can be used to screen for factors (such as solvents, small molecule drugs, peptides, and polynucleotides) or environmental conditions (such as culture conditions or manipulation) that affect the characteristics of activated or aberrant cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In certain aspects of this invention, cells programmed to the hematopoietic lineage play the role of test cells for standard drug screening and toxicity assays, as have been previously performed on hematopoietic cells and precursors in short-term culture. Assessment of the activity of candidate pharmaceutical compounds generally involves combining the hematopoietic cells or precursors provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on hematopoietic cells or precursors, or because a compound designed to have effects elsewhere may have unintended effects on hematopoietic cells or precursors. Two or more drugs can be tested in combination (by combining with the cells either simultaneously or sequentially), to detect possible drug-drug interaction effects.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development of Bidirectional CREB Reporter

A calcium sensing reporter was built around a core bidirectional enhancer composed of tandem CREB (cAMP response element binding protein) binding sites (also known as CRE sites) (FIG. 1). Thus, the enhancer is activated by CREB phosphorylation resulting from elevated intracellular calcium. In neurons, various stimuli lead to CREB phosphorylation. In non-neuronal cells, CREB is phosphorylated in response to growth factors, other transforming agents and inflammation.

The CREB sites were put under the control of cytomegalovirus (CMV) immediate early (IE) promoter as well as bacterial protein binding sites for independent regulation or gating of activity-dependent gene expression in each direction from the core enhancer/promoters. The protein binding sites that were used for gating were the ETR operator sequence which binds to erythromycin resistance repressor protein (mphR) and the tetO operon which binds to the Tet Repressor Protein (TetR). As the CREB reporter system was initially characterized in the brain, the mphR and TetR proteins were put under the control of a brain-specific expression mouse synapsin promoter (mSyn).

The bidirectional CREB activity sensor was then combined with fluorophores GFP and tdTomato or Cre and Flp recombinases (FIG. 1). The schematics of the expression cassettes combined to form the CREB activity sensor are shown in FIG. 1. In addition, photocaging was used for the ligands of the repressor proteins. Green light uncages erythromycin, which relieves Flp (or GFP) from MphR-mediated repression and blue light uncages doxycycline, which relieves Cre (or tdTomato) from TetR-mediated repression. Thus, a CREB activity sensor was developed that allows the detection of activated neurons.

Figure 6:
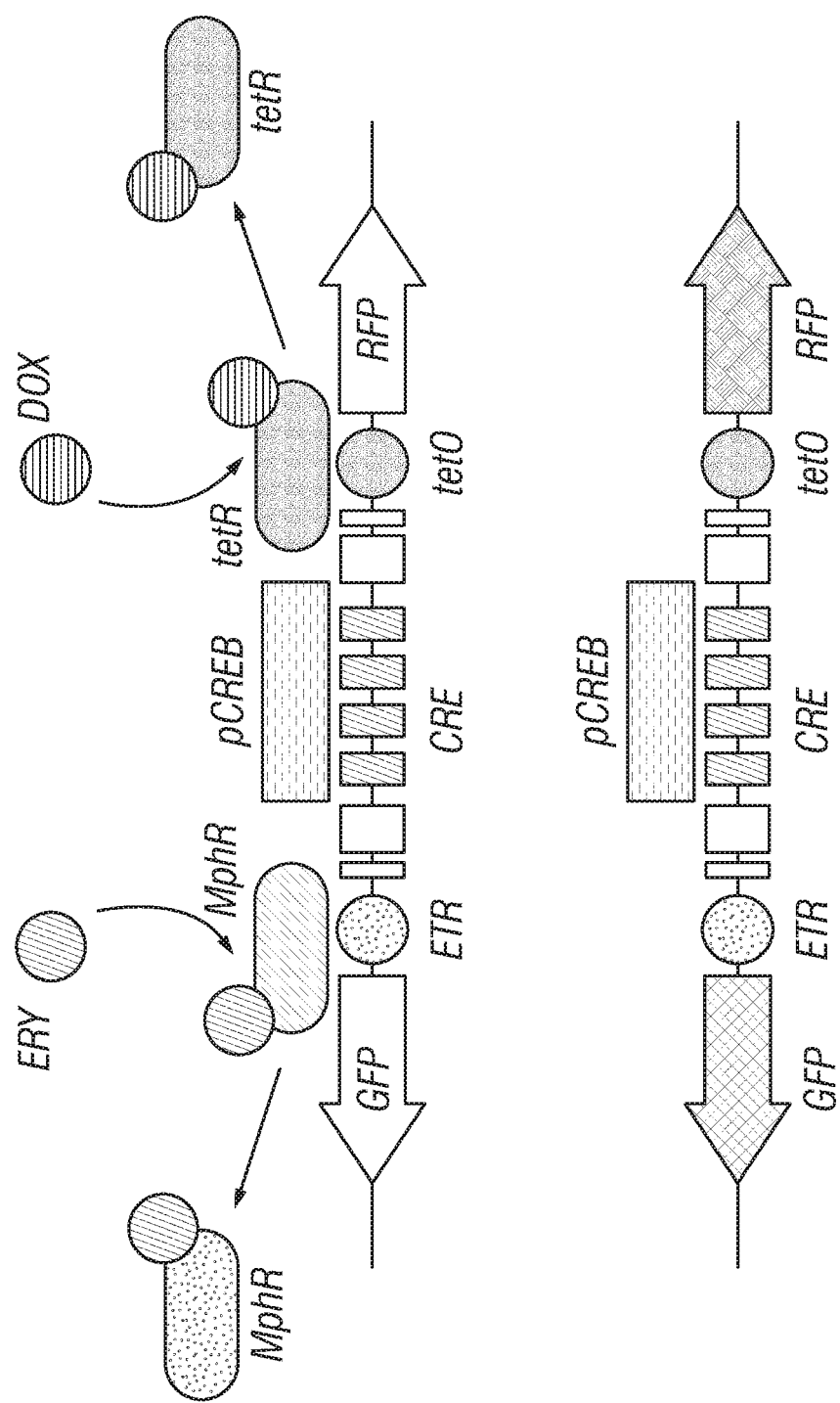
FIG. 6: Bidirectional reporter activity in cultured neurons. Reporter diagram shows a schematic of the constructs used in the studies. Appropriate ligands are required for fluorophore expression in activated neurons. Fluorescence microscopy panels show bidirectional reporter expresses both fluoropheres in neurons activated with forskolin (visible in the far left, middle and far right fields). Repressors block each tag independently. Tag expression is restored when each ligand is added.
Figure 6:
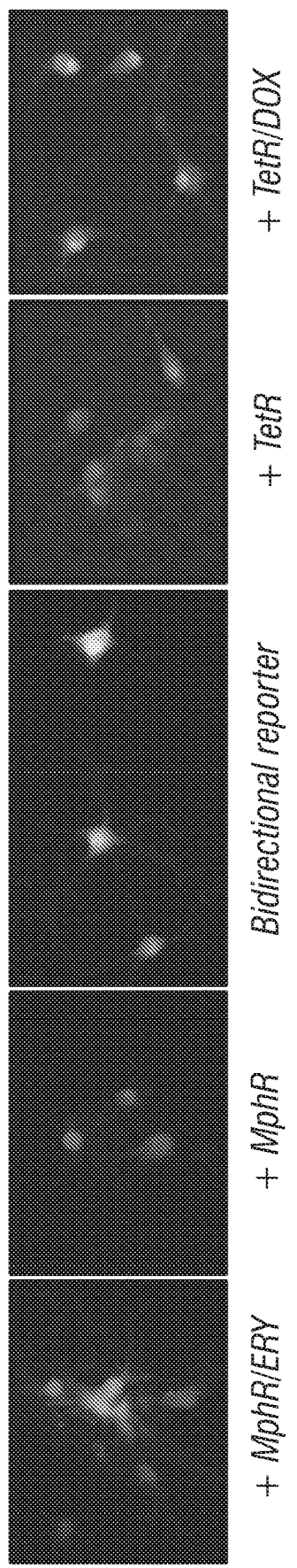
Figure 7A:
FIG. 7A-B: Activity of further reporter constructs tested in vivo. (A) A unidirectional reporter in the mouse dentate gyrus yields more labeled neurons in fear conditioned mice compared to home cage controls. After fixation, sections are stained for c-fos, displaying a subset of double-positive cells (i.e., the two populations do not necessarily overlap due to different regulatory schemes). (B) TetR regulated synapsin promoter constructs expressing GCaMP6 and nls-tdTomato in the mouse visual cortex. Inclusion of TetR virus blocks expression of both proteins. Construct ratio is 1:1 for tdTomato and 1:4 for GCaMP.
Figure 7A:
Figure 7B:
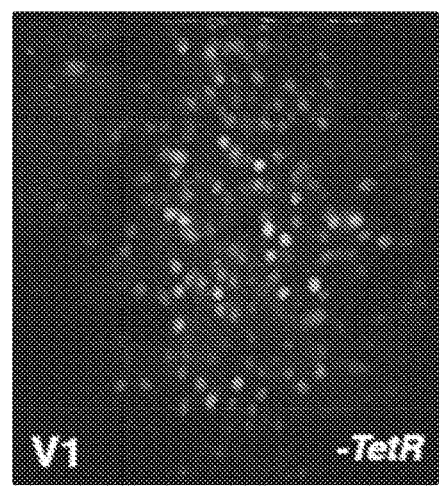
Figure 7B:
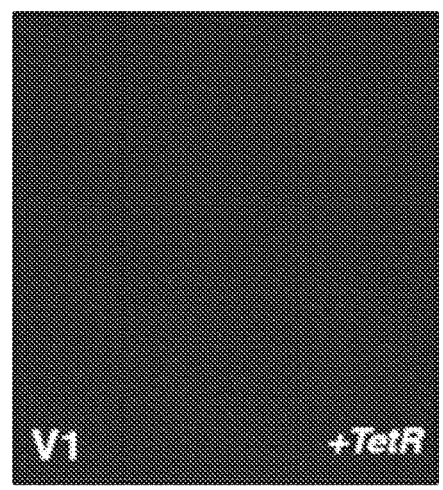

An additional bidirectional CREB activity sensor construct is shown in FIG. 6. In the depicted construct reporter expression is blocked by MphR/TetR or VanR/TetR. Transcription is blocked in activated neurons when the respective repressors are present, but proceeds at pre-repression levels in the presence of the appropriate repressor ligand (see FIG. 6 image panels). Thus, the studies further demonstrate successful incorporation of the expression regulation elements into vectors that could be used for a range of controlled expression systems or in the study of, for example, neuronal gene expression control.

Example 2—Characterization of CREB Reporter System in Brain

Figure 3A:
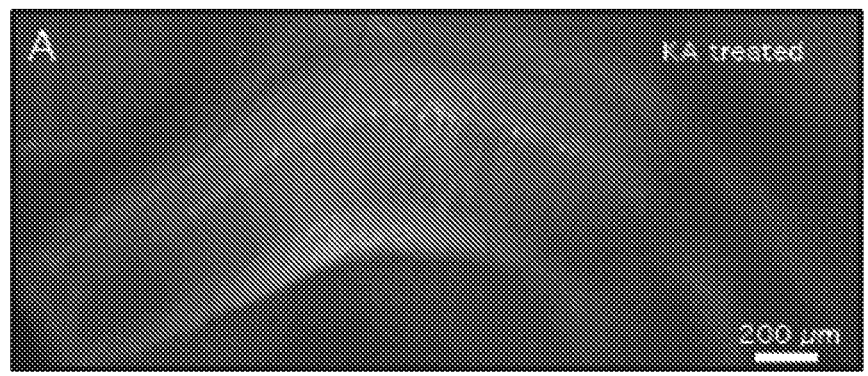
FIG. 3: CREB reporter illuminates neurons activated during epilepsy. Kainate induced seizures produce widespread labeling in the dorsal CA1 pyramidal neurons 30 min after treatment (top) as compared to control animal (bottom).
Figure 3B:
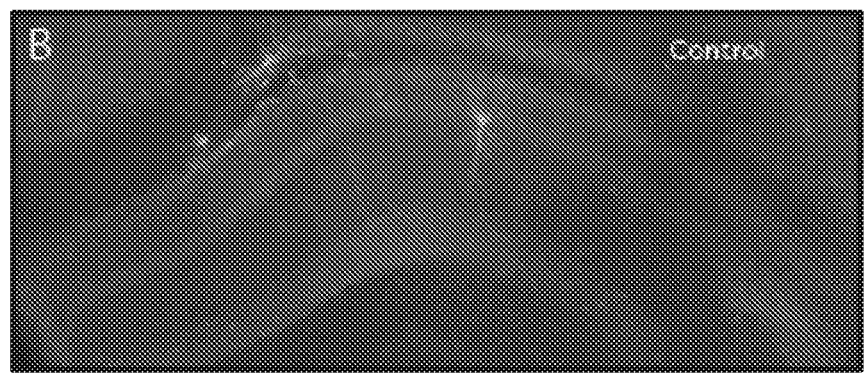

To characterize the bi-directional CREB reporter systems of Example 1, mice were first treated with Kainate to induce seizures and the CREB reporter was able to detect widespread labeling in the dorsal CA1 pyramidal neurons 30 minutes after treatment compared to mice treated with saline (FIG. 3). Thus, the activated neurons could be imaged by administering the CREB reporter.

Figure 4A:
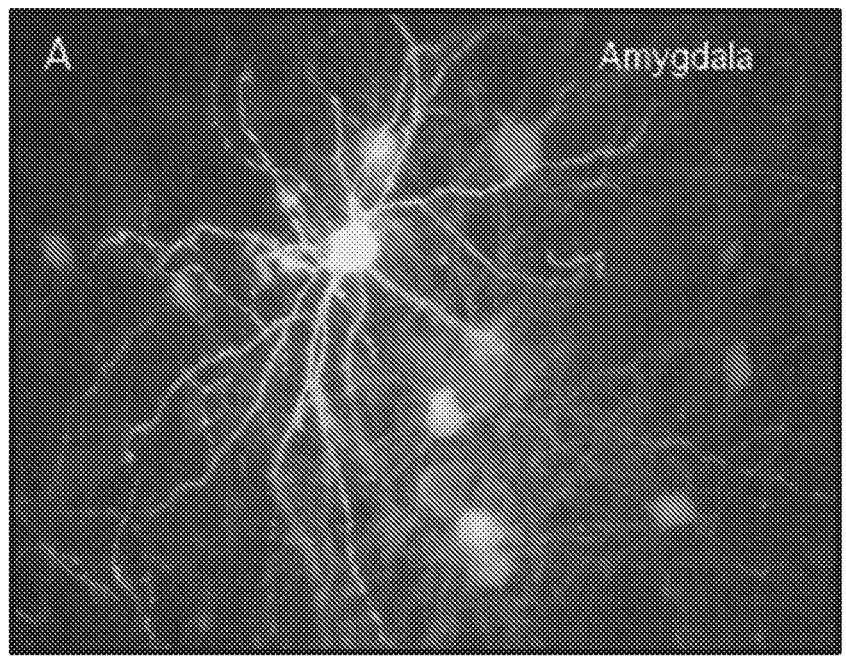
FIG. 4: Dual recombinase reporters in the dentate gyrus and amygdala. (A) Significant label overlap is seen in home cage mice. (B) Nonoverlapping dentate gyrus populations are labeled when reporters are used in different contextual settings.
Figure 4B:
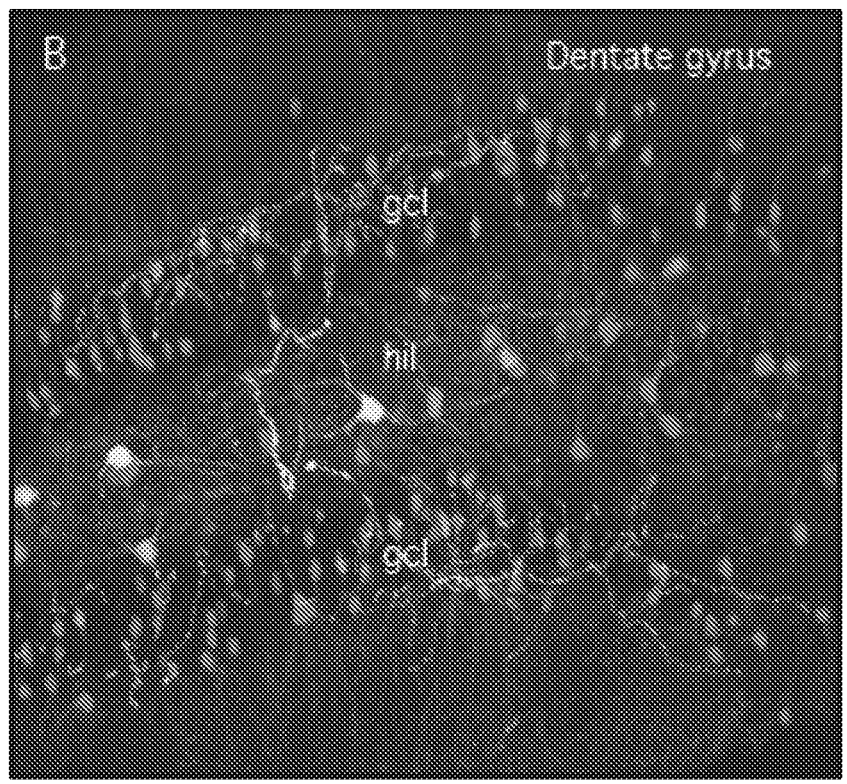

Further in vivo studies demonstrate the activity dual recombinase reporters in the dentate gyrus and amygdala. In FIG. 4A, for instance, significant label overlap is seen in home cage mice. However, nonoverlapping dentate gyrus populations are labeled when reporters are used in different contextual settings (FIG. 4B).

Figure 5A:
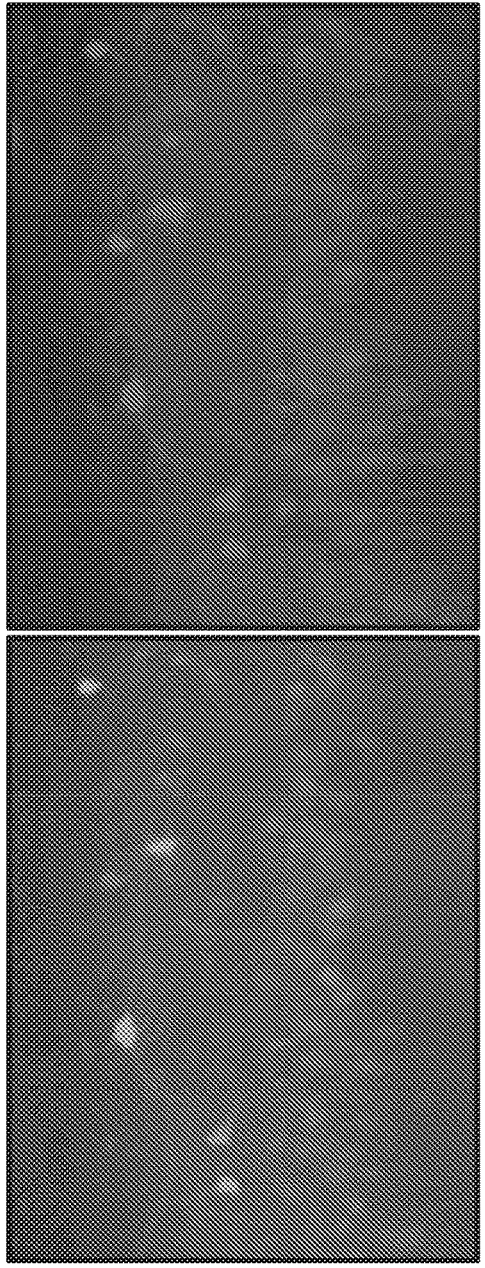
FIGS. 5A-5C: (A) Bidirectional CREB reporter efficiently labels dorsal CA1 hippocampal neurons in vivo. (B) Illustrates CREB reporter labeling dorsal CA1 hippocampal neurons in the presence of TetR to block red fluorophore expression. (C) Six week old female AD model mice injected with the CREB activity reporter. Control mouse (left) and AD mouse (right) illustrate layer-specific changes in reporter expression. More labeled neurons are detected in stratum oriens, stratum pyramidale, and granule and hilus regions of the dentate gyrus in the AD animal.
Figure 5B:
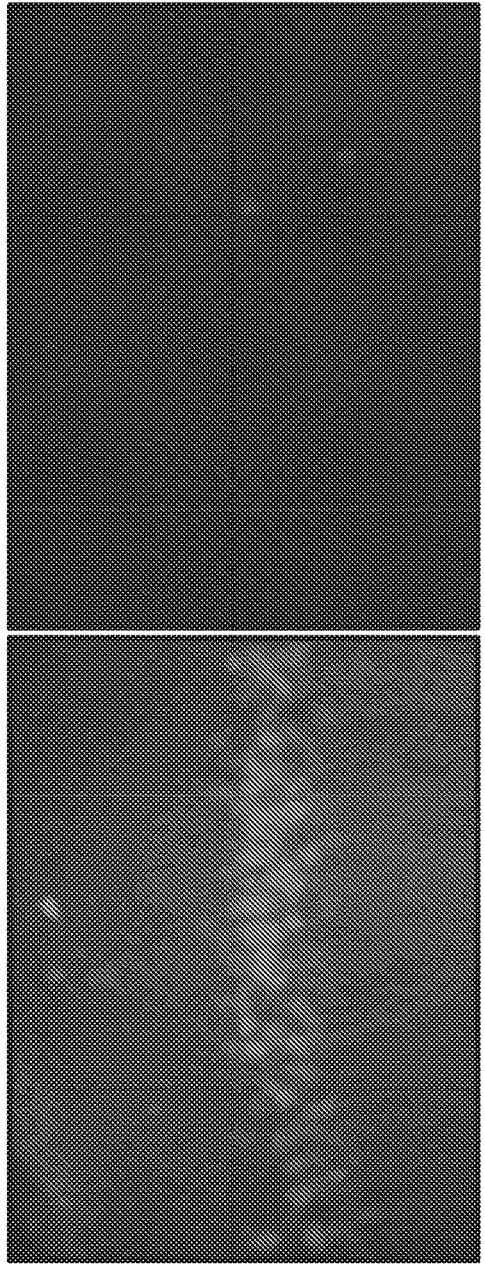
Figure 5C:
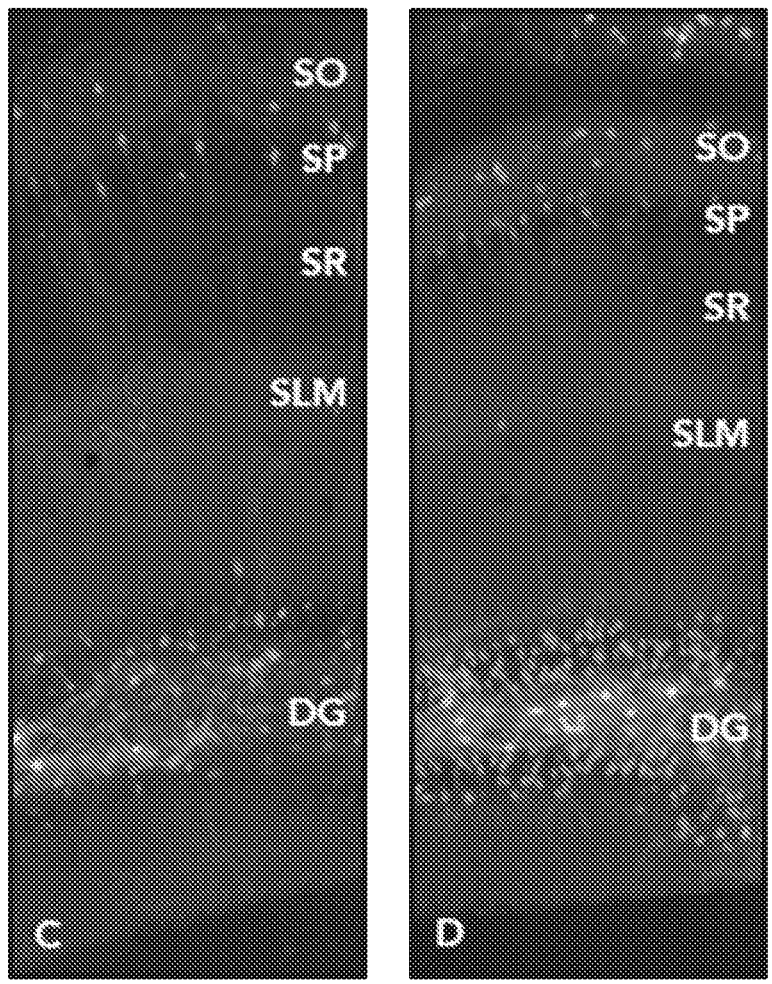

As shown in FIG. 5, bidirectional CREB reporters are able to efficiently label dorsal CA1 hippocampal neurons in vivo (FIG. 5A, right panel). FIG. 5B illustrates CREB reporter labeling dorsal CA1 hippocampal neurons in the presence of TetR to block red fluorophore expression. In the studies of FIG. 5C six week old female Alzheimer's Disease (AD) model mice were injected with the CREB activity reporter. Control mouse (left) and AD mouse (right) illustrate layer-specific changes in reporter expression. More labeled neurons are detected in stratum oriens, stratum pyramidale, and granule and hilus regions of the dentate gyrus in the AD animal. Thus, these studies demonstrate the utility of the duel report systems in the study of clinically relevant disease models.

Further in vivo application of the CREB duel report system are shown in the studies depicted in FIG. 7. As shown in FIG. 7, appropriate viruses have been produced and injected into the mouse hippocampus or cortex. In the absence of repressor, reporter expression is elevated in fear conditioned animals compared to home cage controls (FIG. 7A). This demonstrates reporter function in vivo, significantly when neurons are stimulated physiologically, rather than pharmacologically. It has also been established that the repressor can block reporter expression (see FIG. 7B). Because the reporter and repressor are encoded by separate constructs, repressor dose can be varied (e.g., in an injected dosage or in the chow of animals) to optimize the system for efficient repression and ligand-dependent de-repression. In culture, forskolin was used to stimulate neurons. As an alternative in vivo, a reporter linked to a constitutive repressor-regulated promoter was used. Using this construct, it was determined that it is even easier to block reporter expression in vivo (a 1:1 ratio of reporter to repressor in used in FIG. 7B) than in vitro, where an effective ratio is 1:4 (FIG. 7B). The ligand dose can be tuned to an amount needed to restore reporter expression by adding different doses of ligand to mouse chow (provide in the chow at 200 mg/kg), water, as well as using injectable ligand preparations.

Studies will also be undertaken to further examine the reporter in vivo, in rodent and primate modeles. In these experiments, mouse visual cortex is injected with a virus cocktail to introduce GCaMP6 and the activity reporter linked to a degradation tag (to prevent fluorophore accumulation and the requirement for a transcriptional repressor) into cortical layers II-IV. Cranial windows are then positioned over the injection site. After recovery, the mouse receives defined visual stimuli while neuronal activity is imaged. These studies will allow cells to be identified that respond to the visual stimulus, and to monitor the timing and cellular activity level required to visualize the reporter in activated neurons.

Example 3—Further CREB-Based Expression Systems

Further studies have been completed using constructs, such as those detailed above, but only incorporating one or more copies of the CRE half site (CGTCA) separated by spacer sequences. One difference associated with CRE half site versus full-length site is that CREB binding to half site is much more brief, tightening the temporal relationship between cell stimulation and reporter expression. Examples of such sequences including from 1 to 6 CRE half sites and spacer sequence(s) are provided as SEQ ID NOs: 26-31. In some example constructs, a suicide gene can be expressed from a CRE (or CRE half multimeric) promoter/enhancer in a recombinase-dependent fashion to eliminate any transformed cell. Recombinase would only be expressed in target cells, such as glial cells using this promoter and expression regulation system. This system would restrict killing to glia that are transformed while maintaining control over expression of suicide gene and recombinase to optimize selectivity of cell detection and elimination. An example of such a glia-specific promoter is provided as SEQ ID NO: 35.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,030,015
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Patent Publication No. 2005/0260186
U.S. Patent Publication No. 2006/0104968
U.S. Patent Publication No. US20040146987
PCT Application No. 95/06128
PCT Application No. 94/09699
EP1507865

What is claimed is:

1. An expression vector comprising a bidirectional synthetic CRE enhancer operably linked to:
    (i) a first promoter operably linked to a first expressible gene positioned 3' relative to the bidirectional synthetic CRE enhancer; and
    (ii) a second promoter operably linked to a second expressible gene positioned 5' relative to the bidirectional synthetic CRE enhancer,
    wherein the bidirectional synthetic CRE enhancer comprises at least 2 CRE palindromic sequences separated by a spacer sequence;
    wherein the bidirectional synthetic CRE enhancer comprises one or more CRE half site sequences (CGTCA) that can affect the temporal expression of the first expressible gene or the second expressible gene; and
    wherein the first promoter and the second promoter comprise different operator elements that can support independent ligand-dependent expression gating.

2. The expression vector of claim 1, wherein the spacer sequence comprises 10 to 200 nucleotides.

3. The DNA expression vector of claim 1, wherein the spacer sequence comprises 20 to 100 nucleotides.

4. The expression vector of claim 1, wherein the first promoter and/or the second promoter is a minimal promoter.

5. The expression vector of claim 4, wherein the first promoter and/or the second promoter is selected from the group consisting of minimal CMV promoter, a minimal Na/K ATPase promoter or a minimal Arc promoter.

6. The expression vector of claim 1, wherein the first promoter and/or the second promoter is a cell or tissue type specific promoter.

7. The expression vector of claim 6, wherein the first promoter and/or the second promoter is neuron specific promoter comprises a neuron-specific silencing element.

8. The expression vector of claim 1, wherein the first promoter and/or the second promoter is positioned 10 to 200 nucleotides from the bidirectional synthetic CRE enhancer.

9. The expression vector of claim 1, wherein the first promoter and/or the second promoter is positioned 20 to 100 nucleotides from the bidirectional synthetic CRE enhancer.

10. The expression vector of claim 1, wherein one or both of the operator elements is positioned 10 nucleotides after a TATA box of the first promoter and/or the second promoter.

11. The expression vector of claim 1, wherein one or both of the operator elements comprises 2 to 8 operator binding sites.

12. The expression vector of claim 1, wherein the first promoter and/or the second promoter comprises one or more TET, VAN or ETR element.

13. The expression vector of claim 1, wherein the first expressible gene and/or the second expressible gene encodes a reporter polypeptide, an ion channel polypeptide, a cytotoxic polypeptide, an enzyme, a cell reprogramming factor, a drug resistance marker, a drug sensitivity marker or a therapeutic polypeptide.

14. The expression vector of claim 13, wherein the reporter polypeptide is a fluorescent or luminescent polypeptide.

15. An expression vector comprising a bidirectional synthetic CRE enhancer operably linked to:
 (i) a first promoter operably linked to a first expressible gene positioned 3' relative to the bidirectional synthetic CRE enhancer; and
 (ii) a second promoter operably linked to a second expressible gene positioned 5' relative to the bidirectional synthetic CRE enhancer,
 wherein the bidirectional synthetic CRE enhancer comprises at least 2 CRE half site sequences (CGTCA) sequences separated by a spacer sequence, and
 wherein the first promoter and the second promoter comprise different operator elements that can support independent ligand-dependent expression gating.

16. A method of assessing the status of a cell comprising:
 (a) expressing in the cell a vector; and
 (b) detecting the expression of said first expressible gene and/or said second first expressible gene, thereby assessing the status of the cell; wherein the expression vector comprising a bidirectional synthetic CRE enhancer operably linked to:
  (i) a first promoter operably linked to a first expressible gene positioned 3' relative to the bidirectional synthetic CRE enhancer; and
  (ii) a second promoter operably linked to a second expressible gene positioned 5' relative to the bidirectional synthetic CRE enhancer, and
 wherein the bidirectional synthetic CRE enhancer comprises at least 2 CRE palindromic sequences separated by a spacer sequence.

17. The method accordingly to claim 16, wherein one of said first expressible gene or said second expressible gene encodes a fluorescent or luminescent polypeptide and wherein detecting the expression comprises imaging the cell to detect expression of the fluorescent or luminescent polypeptide.

* * * * *